United States Patent [19]
Foulkes et al.

[11] Patent Number: 6,013,642
[45] Date of Patent: Jan. 11, 2000

[54] USE OF ESTRONE DERIVATIVES AS STEROID SULPHATASE INHIBITORS

[76] Inventors: Roland Foulkes; John Spencer Emtage; Mark William Bodmer; Martin Rae Wales, all of 216, Bath Road, Slough, Berkshire, United Kingdom, SL1 4EN; Graham Arthur William Rook, Gower Street, London, United Kingdom, WC1E 6BT

[21] Appl. No.: 08/721,987

[22] PCT Filed: Apr. 5, 1995

[86] PCT No.: PCT/GB95/00780

§ 371 Date: Apr. 14, 1997

§ 102(e) Date: Apr. 14, 1997

[87] PCT Pub. No.: WO95/26717

PCT Pub. Date: Oct. 12, 1995

[30] Foreign Application Priority Data

Apr. 5, 1994 [GB] United Kingdom ............... 9406715
May 26, 1994 [GB] United Kingdom ............... 941062
Dec. 20, 1994 [GB] United Kingdom ............... 9425759

[51] Int. Cl.$^7$ ............... A61K 31/66; A61K 31/56
[52] U.S. Cl. ............... 514/141; 514/177; 514/178; 514/182; 514/169; 514/170
[58] Field of Search ............... 514/169, 170, 514/141, 177, 178, 182

[56] References Cited

U.S. PATENT DOCUMENTS 5,281,587  1/1994  Reed ............... 514/169

FOREIGN PATENT DOCUMENTS

WO 93/05064  3/1993  WIPO .

OTHER PUBLICATIONS

Akwa et al. (1992) Biochem. J. 288:959–64.
Birnbock et al. (1990) Biochem. Pharmcol. 39:1709–13.
Blauer et al. (1991) Endocrinology 129:3174–9.
Browne et al. (1992) Am. J. Med. Sci. 303:366–71.
Chang et al. (1993) Biochem. J. 291:429–34.
Daynes et al. (1990) J. Exp. Med. 171:979–96.
Daynes et al. (1990) Eur. J. Immunol. 20:793–802.
Dibbelt et al. (1994) J. Steroid Biochem Mol. Biol. 50:261–6.
Duncan et al. (1993) Cancer Res. 53:298–303.
Hennebold et al. (1994) Endocrinology 135:67–75.
Howarth et al. (1993) Bioorganic Med. Chem. Lett. 3:313–8.
Howarth et al. (1994) J. Med Chem. 37:219–21.
Khalil et al. (1994) J. Steroid Biochem. Mol. Bio. 48:545–52.
Labrie et al. (1992) Cancer Res. 52:610–5.
Li et al. (1993) Steroids 58:106–111.
Meikle et al. (1992) J. Steroid Biochem. Mol. Biol. 42:293–304.
Suzuki et al. (1991) Clinical Immunology Immunopathol. 61:202–11.
Waxman, D.J. (1991) Methods in Enzymol. 206:462–76.
Howarth et al.; Estrone Sulfamates; Potent Inhibitors of Estrone Sulfatase with Therapeutic Potential; J. Med. Chem. vol. 37, pp. 219–221, Jan. 1997.

*Primary Examiner*—Theodore J. Criares
*Attorney, Agent, or Firm*—Klauber & Jackson

[57] ABSTRACT

This invention relates to the use of stroid sulphate sulphatase inhibitors which prevent the normal physiological effect of DHEA or related steroids on inflammatory responses.

5 Claims, 17 Drawing Sheets

TIMEPOINT 24HRS

TIMEPOINT 24 HRS

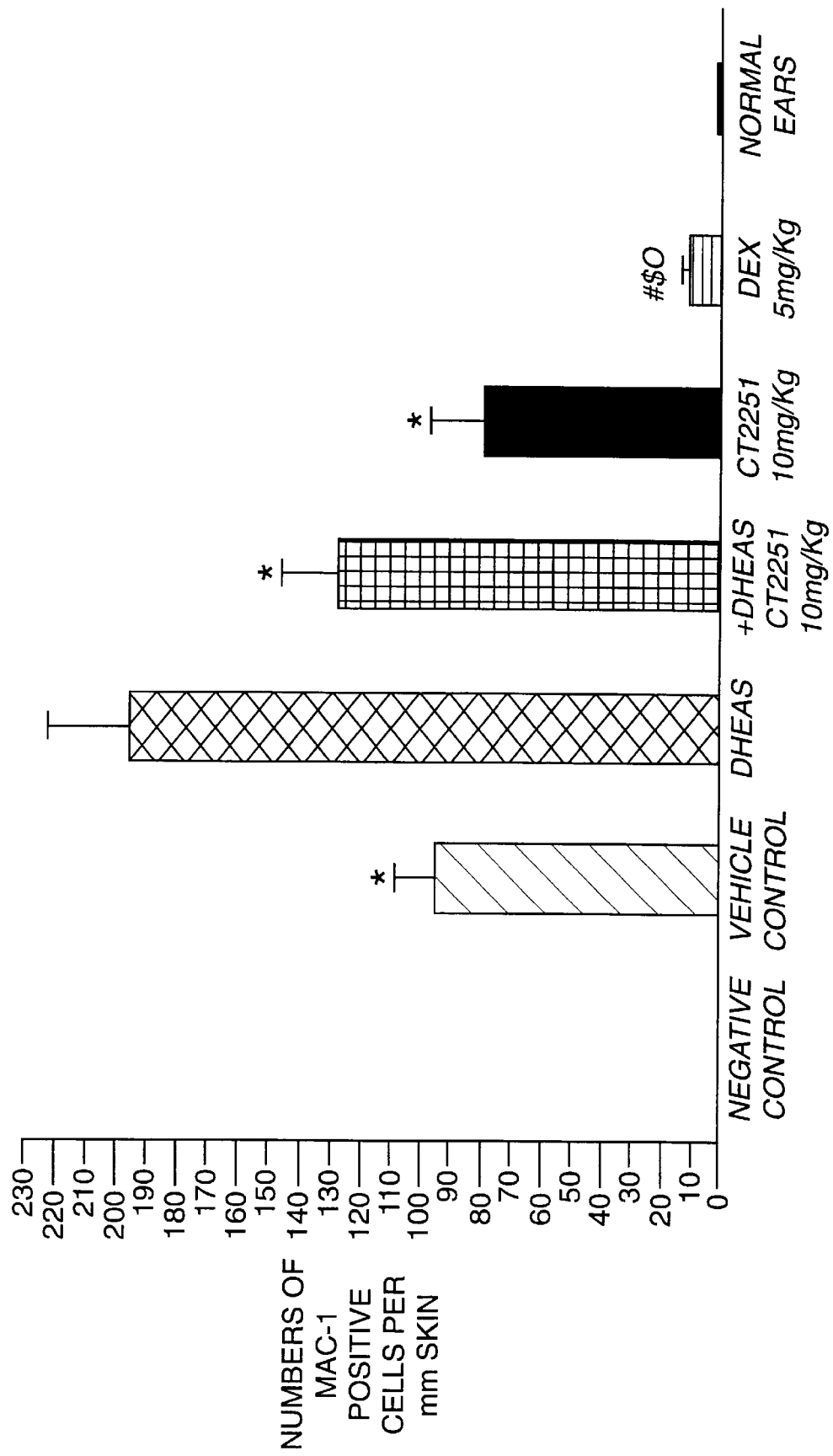

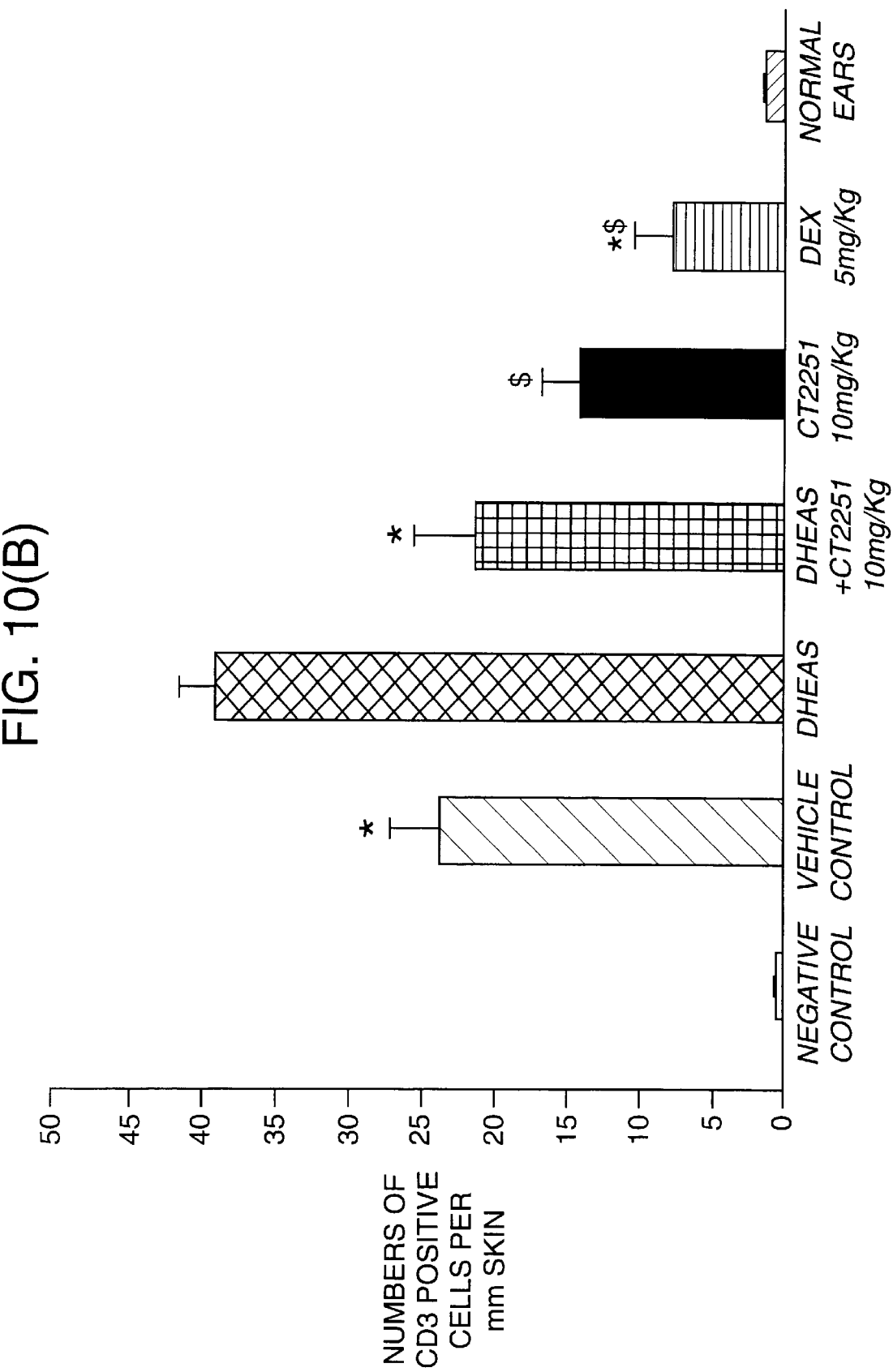

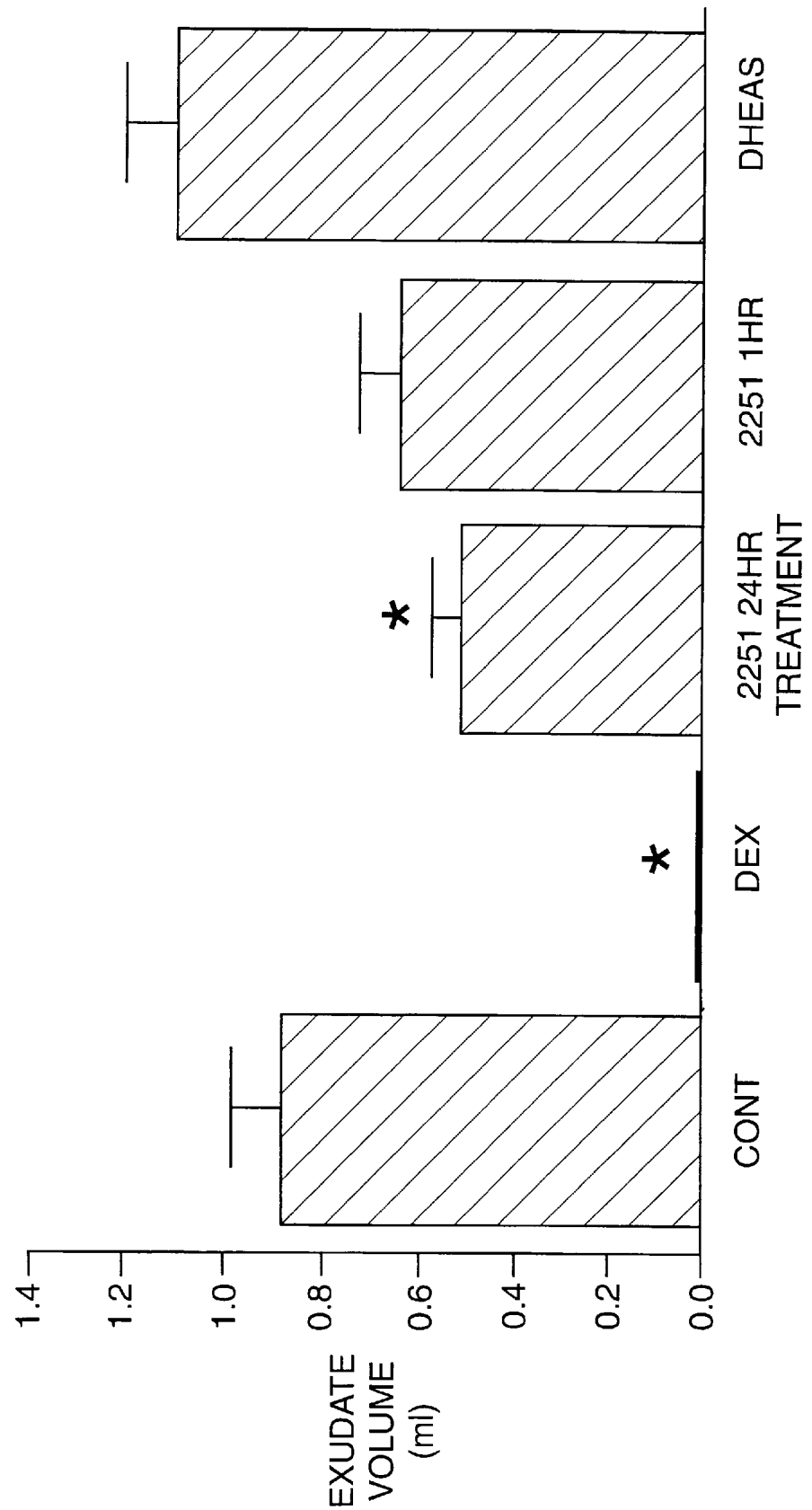

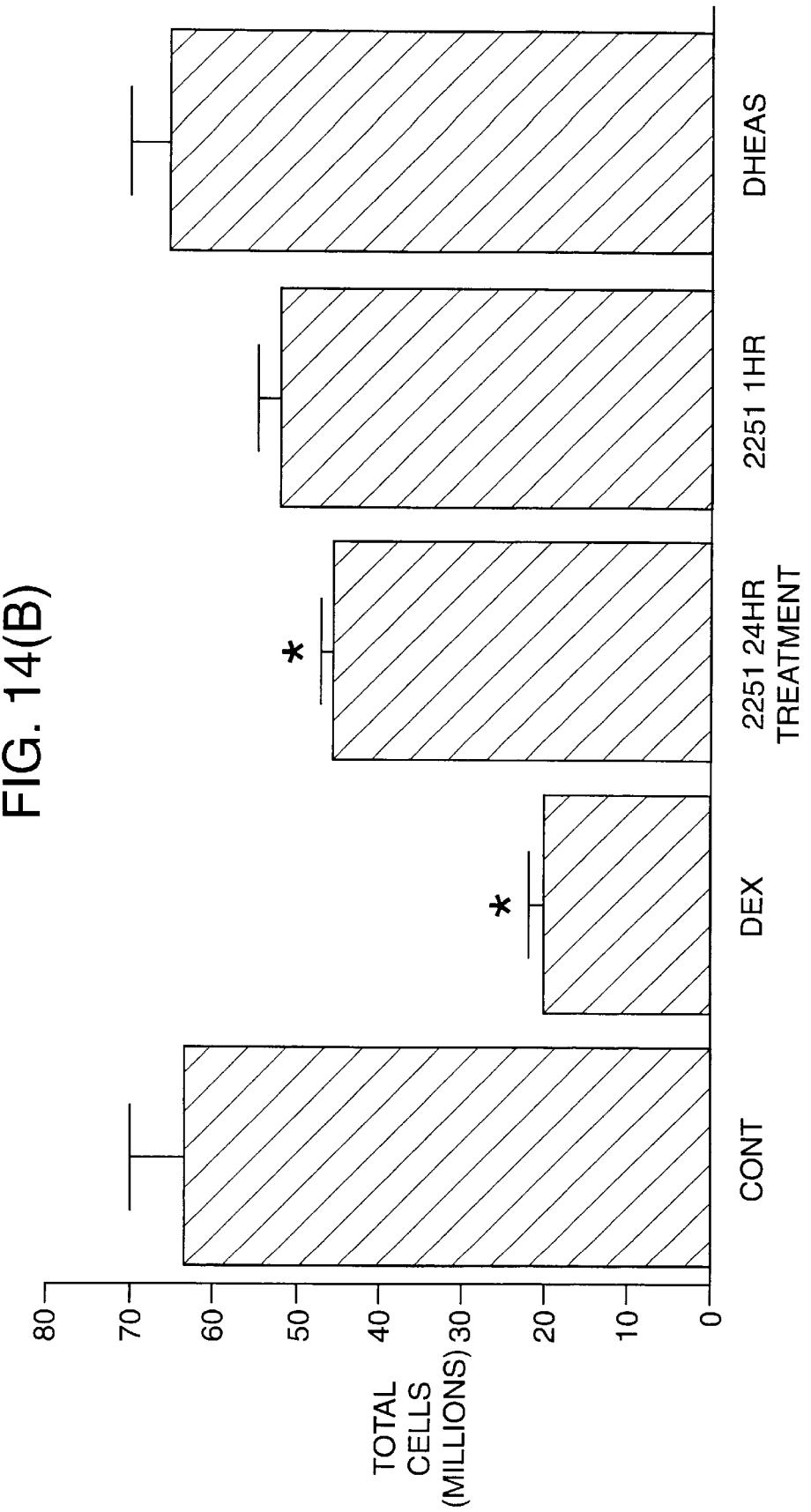

USE OF ESTRONE DERIVATIVES AS STEROID SULPHATASE INHIBITORS

This is a 371 of PCT/GB95/00780 filed 05 Apr., 1995.

FIELD OF THE INVENTION

This invention relates to a new medical use for certain compounds. In particular it relates to the use of inhibitors which prevent the normal physiological effect of DHEA or related steroids on immune and/or inflammatory responses and most especially to the use of inhibitors of a steroid sulphate sulphatase in revealing an endogenous glucocorticoid effect.

BACKGROUND OF THE INVENTION

Dehydroepiandrosterone (DHEA) is a mild androgenic steroid produced by the adrenal cortex and gonads in men and by the gonads in rodents. In all species it is partly under hypothalamo-pituitary control and formed from common steroid precursors. Although DHEA may act as a precursor for more physiologically active androgenic steroids (e.g. testosterone) it is normally secreted as a hormone in its own right. DHEA is rapidly sulphated to DHEA sulphate (DHEAS) before release into the circulation and it is this latter species which constitutes the main circulating form of the steroid. Outside of the CNS DHEAS is itself inactive. To exert physiological effects it must be desulphated by a steroid sulphate sulphatase at the target site and therefore is able to influence local biological events.

Circulating DHEAS levels decline with age (unlike other steroids) and there is some evidence suggesting that exogenous DHEA administration in mice can reverse some of the physiological events associated with the aged phenotype (Daynes et al (1993) The Journal of Immunology, Vol 150: 12, 5219–5230). For example, administration of DHEAS can reverse the increase in IL-6 production in aged mice (Daynes et al (1993) The Journal of Immunology. Vol 150: 12, 5219–5230). In addition, DHEA may regulate insulin sensitivity of adlpocytes and skeletal muscle (Cleary, (1991) P.S.E.B.M. Vol 196: 8–17) However, its major physiological role may be its ability to influence immune responses.

The immune response to antigen is generally either cell mediated (T-cell mediated killing via processed antigens) or humoral (antibody production via recognition of whole antigen). The pattern of cytokine production by $T_H$ cells involved in the immune response can influence which of these response types predominates: cell mediated immunity ($T_{H1}$) is characterised by high IL-2 and IFNg but low IL-4 production, whereas in humoral immunity ($T_{H2}$) the pattern is low IL-2 and IFNg but high IL-4, IL-5, IL-10. Since the secretory pattern is modulated at the level of the secondary lymphoid organ then pharmacological manipulation of the specific TH cytokine pattern can influence the type and extent of the immune response generated.

It is well established that administration of exogenous glucocorticoids to ovalbumin-sensitised mice (and other species) induces immunosuppression in which spleen cells show a reduced capacity to secrete IL-2 but are able to enhance IL-4 secretion upon antigen challenge. In contrast, DHEA or DHEAS administration markedly augments IL-2 and IFNg secretion without affecting IL-4 release (Daynes et al (1990) Eur. J. Immunol. 20 793–802). When DHEA and dexamethasone are co-administered, the DHEA effect predominates which is consistent with DHEA acting as an anti-glucocorticoid in this and other systems (Daynes et al (1990) Eur. J. Immunol. 20 793–802), Browne et al (1992) The American Journal of the Medical Sciences 303 No. 6, 366–371 and Blauer et al (1991) Endocrinology 129 No. 6, 3174–3179). These differing responses of glucocorticoids and DHEA are indicative of $T_{H2}$ and $T_{H1}$ type cytokine patterns respectively, suggesting that they can differentially influence immune responses. Similar effects are seen if spleen cells from sensitized animals are treated with anti-CD3 in the presence of either DHEA, DHEAS or dexamethasone (Daynes et al (1990) J. Exp. Med. 171 979–996).

The immunostimulatory response to biologically inactive DHEAS indicates that there is conversion by steroid sulphate sulphatase within the confines of the secondary lymphoid tissue to the active DHEA. The location of the converting enzyme (steroid sulphate sulphatase) is within the antigen presenting cells (APC) since in purified T cell preparations treated with anti-CD3 antibody. DHEA but not DHEAS could enhance IL-2 production. However, if macrophages were added to the system both steroid types could elicit the increased IL-2 response (Daynes et al (1990) J. Exp. Med. 171 979–996). Hence the pattern of cytokine secretion of $T_H$ cells can be regulated within the secondary lymphoid microenvironment under the influence of adrenal steroids with DHEA promoting cell mediated ($T_{H1}$) type responses. This effect would be counter-regulatory to the normal effect of endogenous glucocorticoids (inhibiting cell-mediated type responses). Indeed, a high affinity binding site for DHEA has been described in murine T cells that is distinct from the T-cell glucocorticoid receptor (Melkle et al (1992) J. Steroid Biochem. Molec. Biol. 42 No. 3/4, 293–304). Furthermore, many of these observations of steroid effects on immune responses in mice have also been demonstrated using human cells (Suzuki et al (1991) Clinical Immunology and Immunopathology 61, 202–211).

$T_{H1}$ and $T_{H2}$-dependent responses show some degree of anatomical compartmentalisation; those lymphoid areas draining non-mucosal sites (e.g. spleen, peripheral lymph nodes) generate predominantly $T_{H1}$ cytokine secreting patterns and those draining mucosal sites (eg Peyer's patches) show $T_{H2}$ type responses. Indeed, anti-CD3-treated cells taken from spleen, peripheral lymph nodes or Peyer's patches from sensitised mice treated with DHEA show typical increased IL-2 and IFNg secretion but only spleen cells or peripheral lymph node cells do so when DHEAS was the treatment. In fact cells from Peyer's patches do not increase IL-2 production following DHEAS treatment but show a high IL-4 and low IL-2 secretion typical of a $T_{H2}$ (and glucocorticoid) type response. This differential influence of DHEA on $T_H$ cell cytokine production correlates with the presence of DHEAS sulphatase in these areas; for example, brachial and axially lymph nodes (non-mucosal) have 6× the DHEAS sulphatase activity than Peyer's patches (mucosal; (Daynes et al (1990) J. Exp. Med. 171 979–996). Hence, in lymphoid areas where generally cell mediated immune responses take place then T cell cytokine production is influenced by locally produced DHEA whereas in areas governing humoral responses. DHEA has less influence allowing effects of circulating glucocorticoids to predominate. Any effects of DHEA are relatively discrete since it is rapidly resulphated on the first-pass through the liver. It follows therefore that in diseases where increased cellular immunity to specific antigens is pathological (e.g. autoimmunity) then a reduction in the influence of DHEA on these responses should lead to a state of relative immunosuppression with humoral immunity being spared.

We believe that inhibition of steroid sulphate sulphatase within the macrophage or other antigen presenting cells would lead to a decreased ability of sensitised T cells to mount a $T_{H1}$ (high IL-2, IFNg low IL-4) response. The normal regulatory influence of other steroids such as glucocorticoids would therefore predominate.

Inhibitors which prevent the normal physiological effect of DHEA or related steroids thereby prevent DHEA or related steroids acting as an anti-glucocorticoid and consequently reveal an endogenous glucocorticoid-like effect. Since glucocorticoids can act on inflammatory processes as well as immune processes this endogenous glucocorticoid-like effect may therefore be manifested as an anti-inflammatory response.

DESCRIPTION OF ASPECTS OF THE INVENTION

In a first aspect the invention provides a therapeutic method for revealing an endogenous glucocorticoid-like effect in a human being which comprises administering an effective amount of an inhibitor which prevents the normal physiological effect of DHEA or related steroids on immune and/or inflammatory responses to said human being.

As used herein the term 'DHEA or related steroids' is used to denote DHEA and physiologically active metabolites of DHEA such as, for example, 7OH-DHEA. Androstenediol (AED), Androstenetriol (AET) and 16OH-DHEA.

In a second aspect the invention provides an inhibitor which prevents the normal physiological effect of DHEA or related steroids on immune and/or inflammatory responses for use in revealing an endogenous glucocorticoid-like effect.

In a third aspect the invention provides an inhibitor which prevents the normal physiological effect of DHEA or related steroids on immune and/or inflammatory responses for use in a method of treatment of a human subject said method of treatment comprising revealing an endogenous glucocorticoid-like effect.

In a fourth aspect the invention further provides the use of an inhibitor which prevents the normal physiological effect of DHEA or related steroids or immune and/or inflammatory responses in the manufacture of a medicament for revealing an endogenous glucocorticoid-like effect.

The inhibitors are believed to achieve their therapeutic effect by removing a counter regulatory pathway which exists in vivo via the effect of DHEA or related steroids thereby revealing an endogenous glucocorticoid-like effect.

The endogenous glucocorticoid-like effect may have an anti-inflammatory and immunosuppressive component. By acting to reveal an endogenous glucocorticoid-like effect the inhibitors produce indirectly immunosuppression and/or an anti-inflammatory response.

The medicament manufactured according to the method of the present invention may be used to prevent or treat any physiological conditions which are generally associated with inflammatory diseases and/or diseases requiring immunosuppression.

The diseases suitable for treatment with the inhibitor which prevents the normal physiological effect of DHEA or related steroids on immune and/or inflammatory responses according to all aspects of the invention disclosed herein are preferably those resulting from autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema, asthma and organ rejection following transplantation.

The effect of the inhibitor in revealing an endogenous glucocorticoid-like effect may be determined by measuring anti-inflammatory and/or immunosuppressive responses.

The inhibitors which prevent the normal physiological effect of DHEA or related steroids on immune and/or inflammatory responses for use according to the invention may for example be a steroid analogue, a steroid derivative or fragment, a chemical compound or an antibody against DHEA or a related steroid, or a receptor therefor.

The inhibitors which prevent the normal physiological effect of DHEA or related steroids on immune and/or inflammatory responses may be inhibitors of a steroid sulphate sulphatase (E.C. 3.1.6.2). As used herein the term 'a steroid sulphate sulphatase' denotes an enzyme which can remove a sulphate group from a sulphated steroid. Such an enzyme may be for example aryl sulphatase C (E.C. 3.1.6.1) or may desirably be one specific for DHEAS or related sulphated steroids i.e. sulphated metabolites derivable from DHEAS.

The inhibitors for use in the present invention are preferably steroid sulphate sulphatase inhibitors and most preferably are specific for DHEAS (or related sulphated steroids) sulphatase.

Examples of steroid sulphate sulphatase inhibitors are described in Howarth et al (J. Med. Chem (1994) 37, 219–221; and Bioorganic and Medicinal Chemistry Letters (1993) 3 (2) 313–318), Endocrinology (1991) 129 No. 6, 3174–3179) Birnbock and von Angerer (1990) (Biochemical Pharmacology 39 (11), 1709–1713); U.S. Pat. No. 5,281,587; Duncan et al (1993) (Cancer Research 53, 298–303); Li et al (1993) (Steroids 58, 106–111); Dibbelt et al (1994) (J. Steroid Biochem Molec. Biol. 50, 5/6, 261–266).

The inhibitors which prevent the normal physiological action of DHEA on immune and/or inflammatory responses via its physiologically active metabolites may be for example inhibitors of the enzymes 17-ketosteroid reductase, 16-α hydroxylase and 7-hydroxylase preferably 7-α -hydroxylase.

As indicated above the 7-hydroxylase is preferably 7α-hydroxylase. The 7α-hydroxylase is cytochrome P450 dependent (Khalil et al J. Steroid Biochem. Mol. Biol. 48, 5/6 545–552, (1994)) and is widely distributed i.e. brain, pituitary, adrenal skin, adipose tissue, lymphocytes and lung and is distinct from the testicular and hepatic testosterone/ androstenedione 7α-hydroxylases, or the known hepatic cholesterol 7α-hydroxylases. The 7α-hydroxylase inhibitors for use according to the invention are therefore specific for the 7α-hydroxylases derived for example, from brain, pituitary, adrenal, adipose tissue, lymphocytes, skin and lung tisse and do not inhibit the testicular and hepatic testosterone/androstenedine 7α-hydroxylases or the known hepatic cholesterol 7α-hydroxylase.

7-hydroxylase inhibitors may be assayed for example in an enzyme assay for 7α-OH dehydroepiandrosterone and dehydroepiandrosterone or dehydroepiandrosterone sulphate and 7α-OH dehydroepiandrosterone sulphate. Such enzyme assays are known in the art, see for example Khalil et al (1994) (J. Steroid Biochem. Molec. Biol. 48, 5/6 545–552). Inhibitors of 7-hydroxylase may be evaluated by adding at various concentrations to the above assay. The biological activity of the 7-hydroxylase inhibitors identified as above to inhibit ongoing immune responses in cellular (eg MLR) and in vivo (e.g. DTH) systems will be studied as described more fully herein.

Similarly 16α-hydroxylase and inhibition thereof may be assayed by following the above teaching for steroid sulphate sulphatase and 7α-hydroxylase and as described by Chang et al; (1993) (Biochem J. 291, 429–434) after Waxman D. J. (1991) (Methods in Enzymol 206 462–476). 17 ketosteroid reductase and inhibition thereof would be assayed by following the above teaching for steroid sulphate sulphatase and 7α-hydroxylase and as described by Labrie et al (1992) Cancer Res 52 (3) 610–615 using a suitable source of enzyme activity.

Interconversion of DHEA, AED, 7OH, DEA, AET and 16OH DHEA may be assayed by following the teaching of Khalil et al (1994) (J. Steroid Biochem. Molec. Biol. 48 5/6 454–552) or by Alena et al (1992) (J. Steroid Biochem and Molec. Biol. 288 959–964). A suitable source of the appropriate enzyme activity would be used.

Assay systems such as radioimmunoassay kits for measurement of DHEA and DHEA-S are commercially available (see for example Diagnostic Systems Laboratories, 445 Medical Centre Blvd, Webster, Tex. 77598).

Alternatively the anti-glucocorticoid effect could be achieved by for example blocking the target receptor for DHEA or related steroid or transport mechanism for DHEAS or related sulphated steroids. For example inhibitors may work by blocking the DHEA or related steroid receptor present in a T-cell or inhibiting the transport mechanism of DHEAS into cells and may be for example a peptide or antibody molecule.

Inhibitors which inhibit the uptake of DHEAS and related sulphated steroids into cells for example via a transport mechanism may be identified by an assay which would measure the uptake of labelled DHEAS (or related sulphated steroid) into a cell and the effects of inhibitors on such uptake as described more fully herein.

The effect of an inhibitor on the ability of DHEA or related steroids to bind to a receptor such as a T-cell receptor may be measured using techniques well known in the art. For example binding inhibition studies may be carried out measuring the effect of an inhibitor on the ability of the steroid to bind to its receptor.

Where the inhibitor for use in the invention is an antibody molecule it may in general belong to any immunoglobulin class. It may be of animal, for example mammalian, e.g. murine, rat, hamster, or human origin. The antibody may be a whole immunogloblin or a fragment thereof, for example a F(ab')$_2$ or Fab fragment.

An antibody against an enzyme, receptor, or steroid (DHEA or DHEAS or related steroid) may be prepared using well-known immunological techniques employing the enzyme, receptor or steroid as antigen. Any suitable host may, for example, be immunised with the enzyme, receptor or steroid and splenocytes or lymphocytes recovered and immortalised using for example, the method of Kohler et al Eur. J. Immunol. 6 511 (1976). The resulting cells are diluted and cloned to obtain a single genetic line producing antibodies in accordance with conventional practice. Where it is desired to produce recombinant antibodies these may be produced using methods well known in the art.

The antibody may comprise an engineered human antibody e.g. a chimeric antibody or a CDR-grafted antibody as described in our International Patent Application WO-A-91/09967, EP 0120694 and EP 125023 the disclosures of which are incorporated herein by reference.

In a fifth aspect the invention provides a drug for revealing an endogenous glucocorticoid effect comprising an inhibitor which prevents the normal physiological effect of DHEA or related steroids on immune and/or inflammatory responses as an active ingredient.

In a sixth aspect the invention provides a method of treatment of a human subject suffering from a disease said method of treatment comprising revealing an endogenous glucocorticoid-like by administering an effective amount of an inhibitor which prevents the normal physiological effect of DHEA or related steroids on immune and/or inflammatory responses.

According to a seventh aspect there is provided a pharmaceutical composition which comprises an inhibitor which prevents the normal physiological effect of DHEA or related steroids on immune and/or inflammatory responses for use in revealing an endogenous glucocorticoid-like effect in admixture with one or more pharmaceutically acceptable carriers, excipients or diluents.

In a eighth aspect of the invention we provide a method for the manufacture of a pharmaceutical composition for use in revealing an endogenous glucocorticoid-effect effect which comprises admixing an inhibitor which prevents the normal physiological effect of DHEA or related steroids on immune and/or inflammatory responses and one or more pharmaceutically acceptable carriers, excipients or diluents.

Pharmaceutical compositions for use according to the present invention may be formulated in conventional manner, optionally with one or more physiologically acceptable carriers, diluents or excipients.

Inhibitors which prevent the normal physiological effect of DHEA or related steroids on immune and/or inflammatory responses for use according to the present invention may be formulated for oral, buccal, parenteral or rectal administration or in a form suitable for nasal administration or administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methycellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspension, or they may be presented as a dry product for constitution with water or other suitable vehicle before use. Such liquid preparations may be prepared by conventional means with pharmaceutically acceptable additives such as suspending agents; emulsifying agents; non-aqueous vehicles; and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The inhibitor may be formulated for parenteral administration by injection e.g. by bolus injection or continuous infusion. Formulations for injection may be presented in unit dosage form. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The inhibitor may also be formulated in rectal compositions such as suppositories or retention enemas, e.g. containing conventional suppository bases such as cocoa butter or other glycerides.

In addition to the formulations described previously, the inhibitor may also be formulated as a depot preparation. Such long acting formulations may be administered by implantation or by intramuscular injection.

For nasal administration or administration by inhalation the compounds for use according to the present invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas.

The compositions may, if desired, be presented in a pack or dispenser device which may contain one or more unit dosage forms containing the active ingredient. The pack or dispenser device may be accompanied by instructions for administration.

The dose at which the inhibitor which prevents the normal physiological effect of DHEA or related steroids on immune and/or inflammatory responses will be administered will depend on the nature of the inhibitor and the route of administration, the potency of inhibitor and the body weight and pathology of the patient. Dosages may, for example, be in the range 1 μg/kg to 100 mg/kg, preferably 0.1 mg to 10 mg/kg and most preferably 0.1 mg to 1 mg/kg.

As indicated above the inhibitor is preferably an inhibitor of a steroid sulphate sulphatase and preferably of DHEAS (or a related sulphated steroid) sulphatase. Steroid sulphate sulphatase is a microsomal enzyme found in many tissues but predominantly in lymphoid (presumably macrophage) and pituitary tissues (Milewich et al, (1984) J. Steroid, Biochem 21 No. 5, 529–538). It is as yet unclear whether isoforms of this enzyme exist or whether the macrophage enzyme is distinct from that of other tissues. The steroid sulphatase inhibitor is most preferably specific for DHEAS sulphatase found in macrophages or other antigen presenting cells.

As a simple first step to test our hypothesis a couple of structural derivatives of oestrone have been made which inhibit steroid sulphate sulphatase. It will be evident to a man skilled in the art that structural derivatives of DHEA could also be made and assayed as described below. These have been assayed against the enzyme present in macrophage cell lines and isolated human placental sulphatase and then their ability to inhibit ongoing immune response in cellular (eg. Mixed Lymphocyte Reaction [MLR]) and in vivo (eg Delayed type Hypersensitivity [DTH]) systems has been studied. In addition their ability to interfere with DHEAS-mediated T cell IL-2 production in the presence and absence of macrophages has been assayed.

According to a ninth aspect the invention provides a method of screening for an inhibitor which prevents the normal physiological effect of DHEA or related steroids on immune and/or inflammatory responses comprising measuring the ability of said inhibitor to inhibit ongoing immune and/or inflammatory response in cellular and/or in vivo systems.

The effects of inhibitors according to the present invention on inflammation may be measured in vitro using methods known in the art such as, for example, by measuring inflammatory mediator release e.g. cytokine, prostaglandin, thromboxin or PAF release, and in vivo using inflammatory dependent processes such as for example carageenan pleurlsy described more fully herein.

The effect of the inhibitors on immune function may be measured in vitro using methods well known in the art such as in Mixed Lymphocyte Reaction and in vivo in, for example, a Delayed Type Hypersensitivity Reaction.

The screening method is particularly suitable for identifying those inhibitors which prevent the normal physiological effect of DHEA or related steroids on immune and/or inflammatory responses suitable for use in revealing an endogenous glucocorticoid effect.

BRIEF DESCRIPTION OF THE FIGURES

The invention is further illustrated with reference to the following Examples and Figures in which.

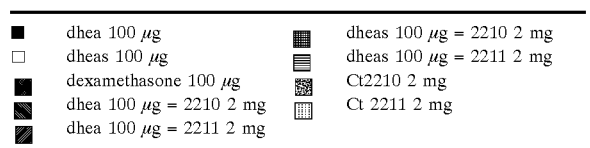

timepoint=48 hr. Steroids given on day 0, 4 and 5 subcutaneously, sensitised with 2.5% oxazalone, challenged with 0.25%.

Figure 5:
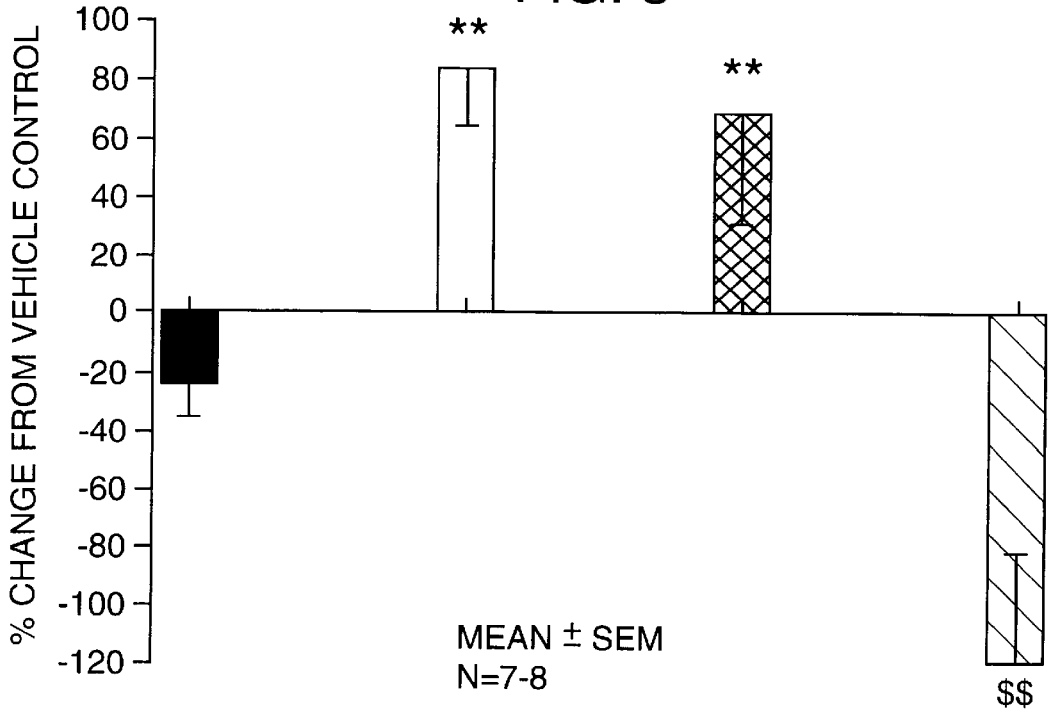

FIG. 5 shows a histogram analysis of contact sensitisation results.

Figure 6:
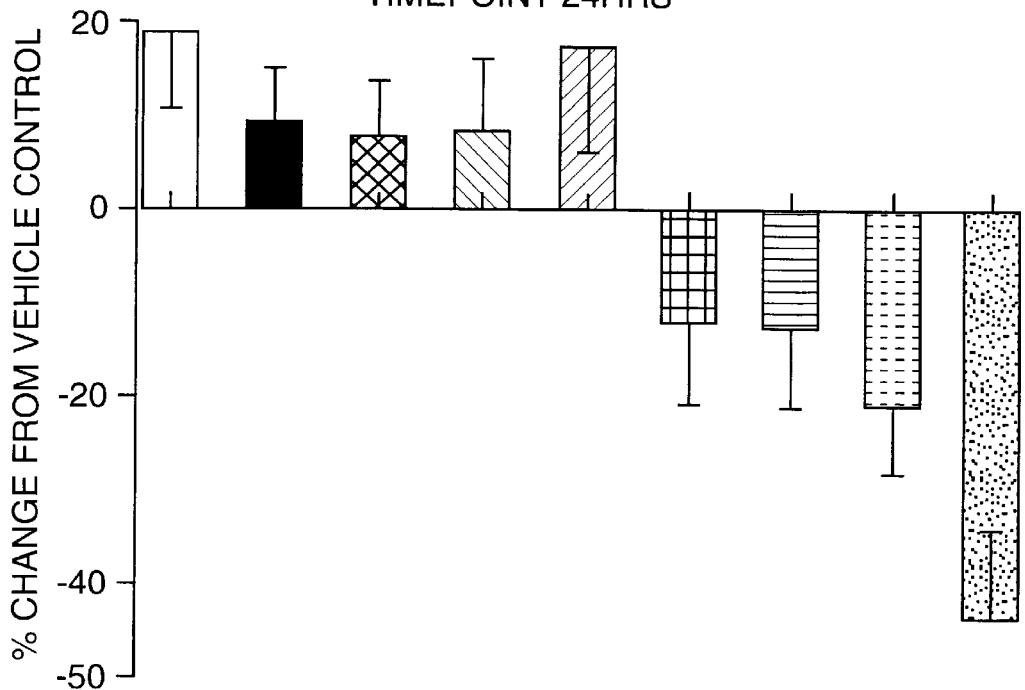

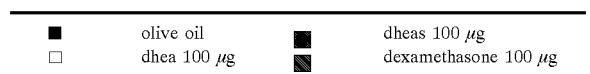

timepoint=24 hr. Steroids given on day 0 and 5 subcutaneously, sensitised with 2.5% oxazalone, challenged with 0.25%.
by anova ** p<0.05 vs control+dexamethasone
$$p<0.05 vs control dhea+dheas FIG. 6 shows a histogram analysis of contact sensitisation results

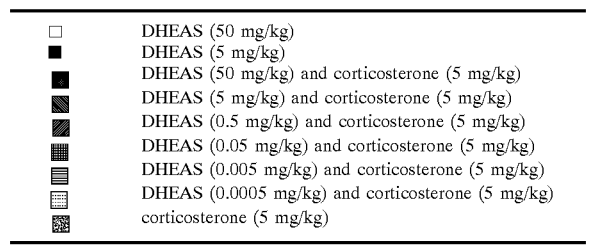

steroids given on day 0 and 4 sub.cut in dmso 20%: olive oil 80% sensitised with 2.5% oxazalone challenged with 0.25%
Results are given as mean±sem, n=10

Figure 7A:
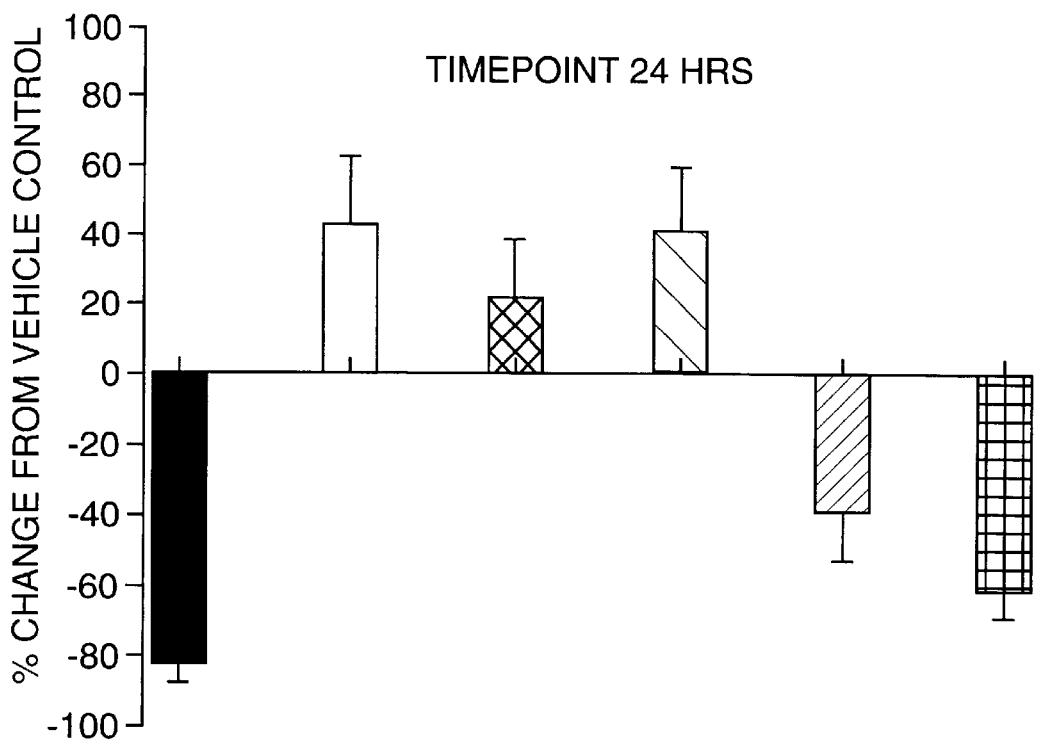
Figure 7B:
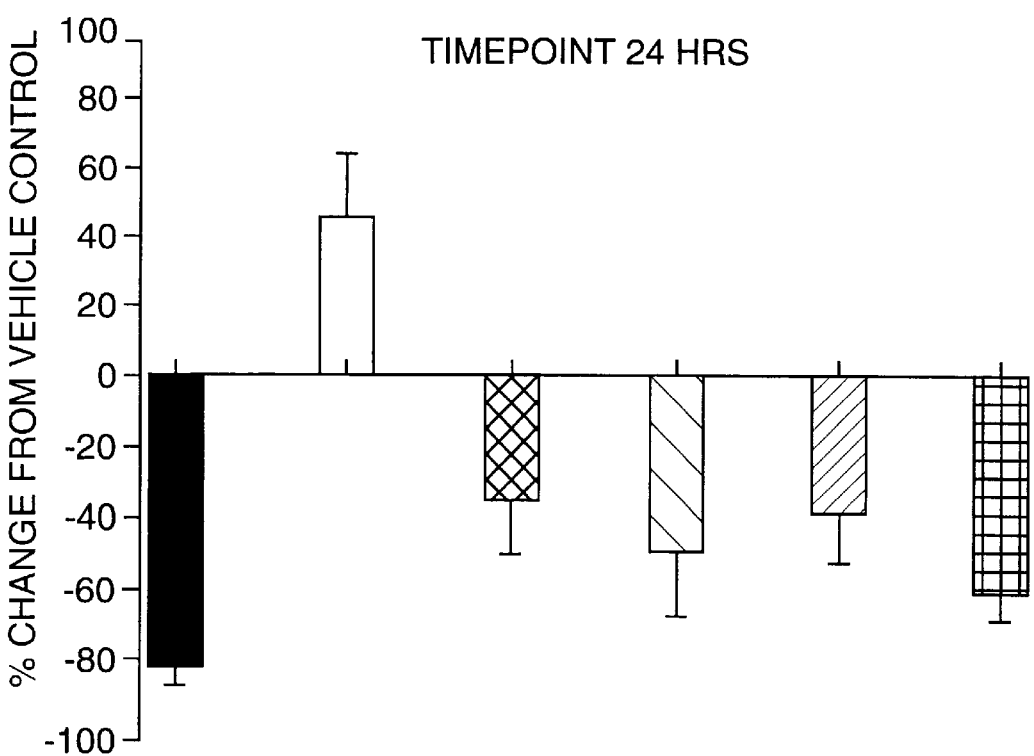

FIG. 7 shows a histogram analysis of contact sensitisation results.

| | | |
|---|---|---|
| A | ■ | dexamthasone 5 mg/kg |
| | □ | DHEA 5 mg/kg |
| | ■ | DHEA 5 mg/kg and Ct 2251 0.1 mg/kg |
| | ▨ | DHEA 5 mg/kg and Ct 2251 10 mg/kg |
| | ▧ | Ct 2251 0.1 mg/kg |
| | ▦ | Ct 2251 10 mg/kg |
| B | ■ | dexamthasone 5 mg/kg |
| | □ | DHEAS 5 mg/kg |
| | ■ | DHEAS 5 mg/kg and Ct 2251 0.1 mg/kg |
| | ▨ | DHEAS 5 mg/kg and Ct 2251 10 mg/kg |
| | ▧ | Ct 2251 0.1 mg/kg |
| | ▦ | Ct 2251 10 mg/kg | steroids were given subcutaneously on days 0 and 4 sensitised with 2.5% oxazalone, challenged with 0.25%.
results given as mean±sem, n=7

Figure 8:
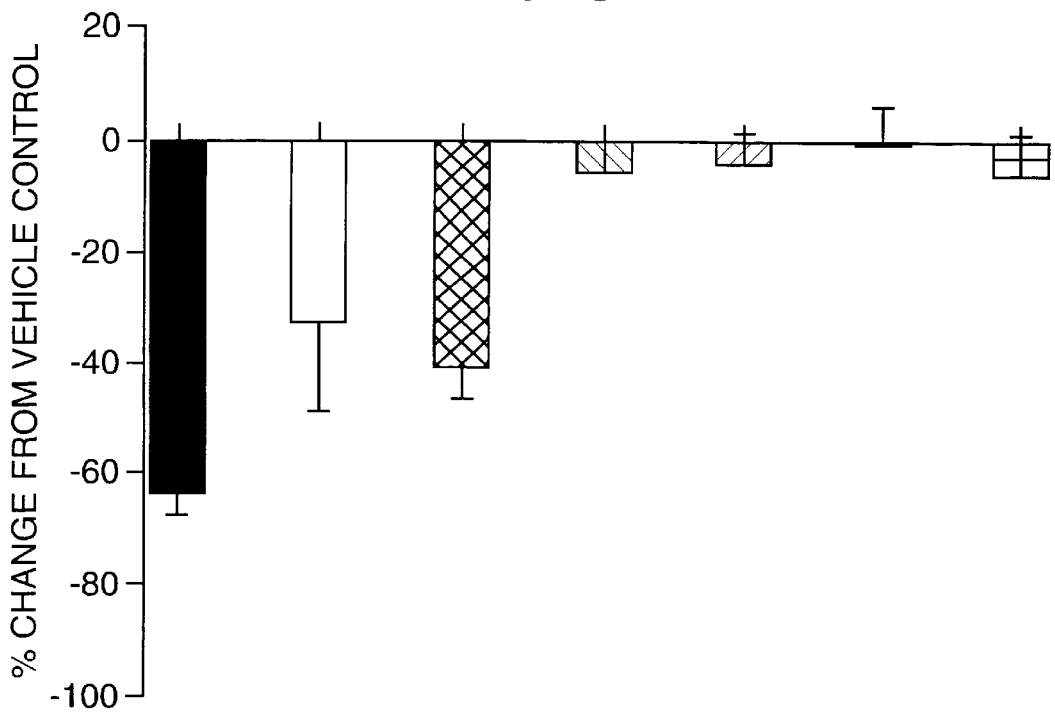

FIG. 8 shows a histogram analysis of contact sensitisation results

| | | | | |
|---|---|---|---|---|
| ■ | dexamethasone 5 mg/kg | | ▨ | Ct 2251 0.01 mg/kg |
| □ | Ct 2251 0.3 mg/kg | | ▦ | Ct 2251 0.003 mg/kg |
| ■ | Ct 2251 0.1 mg/kg | | ▤ | Ct 2251 0.001 mg/kg |
| ▧ | Ct 2251 0.03 mg/kg | | | | time point=24 hours, steroids given on day 0, 4 subcutaneously. Sensitised with 2.5% oxazalone, challenged with 0.25%.
results given as mean±sem, n=7–14

Figure 9:
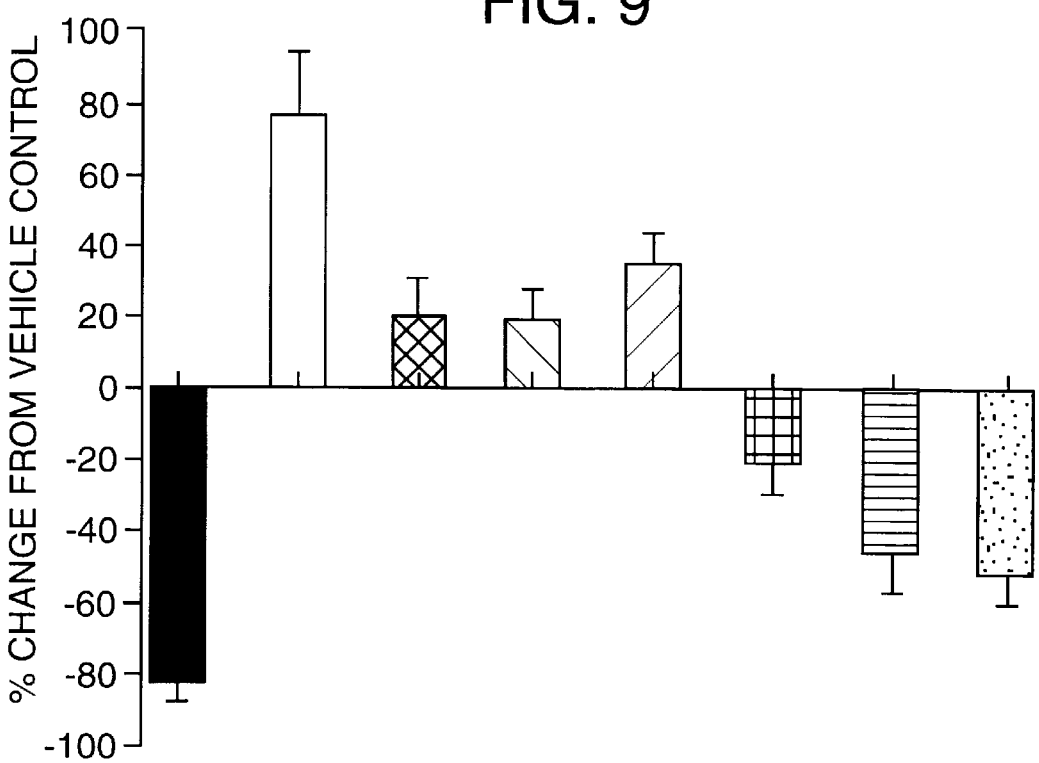

FIG. 9 shows a histogram analysis of contact sensitisation results

| | |
|---|---|
| ■ | dexamthasone 5 mg/kg |
| □ | dheas 50 mg/kg |
| ■ | dheas 15 mg/kg |
| ▨ | dheas 5 mg/kg |
| ▧ | dheas 50 mg/kg and Ct 2251 0.1 mg/kg |
| ▦ | dheas 15 mg/kg and Ct 2251 0.1 mg/kg |
| ▤ | dheas 5 mg/kg and Ct 2251 0.1 mg/kg |
| ▩ | Ct 2251 0.1 mg/kg | time point=24 hours, steroids given on day 0,4 subcutaneously. Sensitised with 2.5% oxazalone, challenged with 0.25%.
results given as mean±sem, n=7–14

FIG. 10 shows effect of Ct 2251 on macrophage and T-cell numbers in contact sensitisation experiments in mice

Figure 11A:
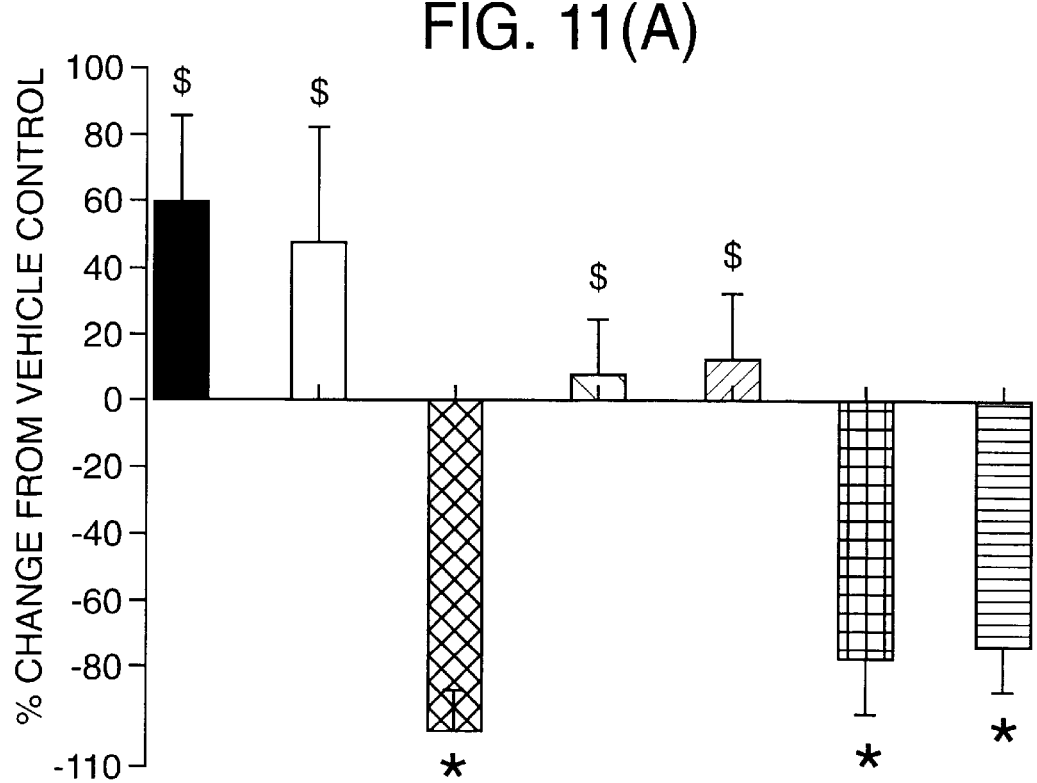
Figure 11B:
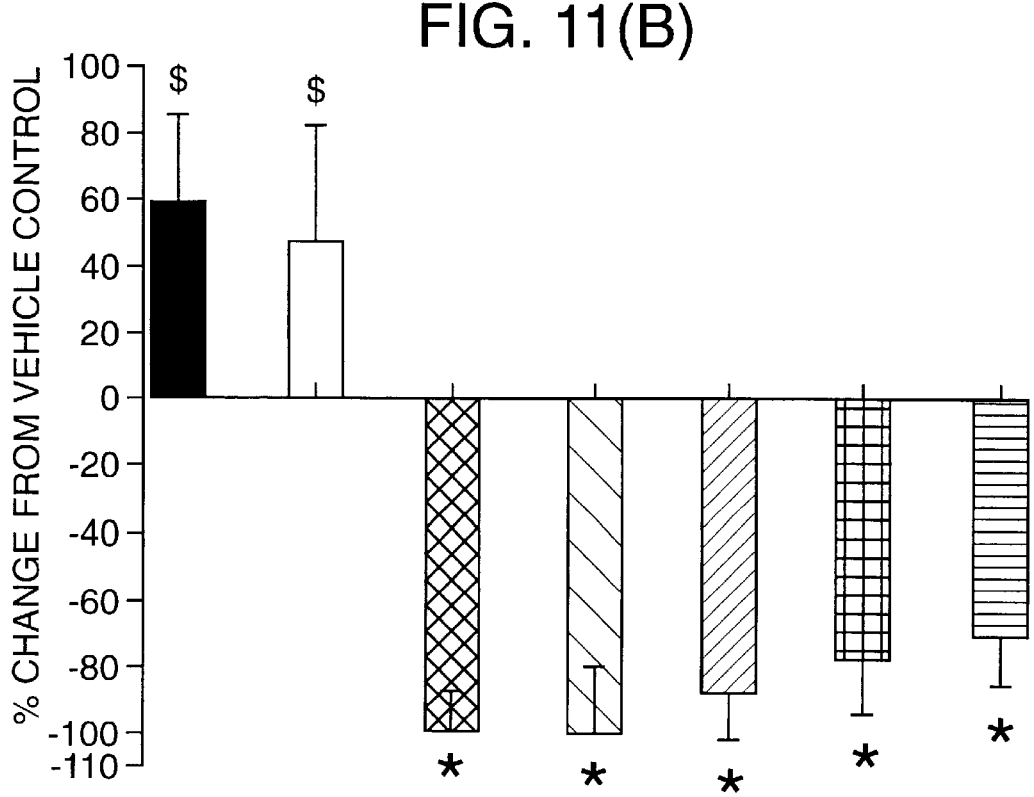

| | | | | |
|---|---|---|---|---|
| A | ▨ | vehicle control | ■ | Ct 2251 10 mg/kg |
| | ■ | DHEAS | ▤ | DEX 5 mg/kg |
| | ▦ | DHEAS and Ct 2251 10 mg/kg | | |
| B | □ | negative control | ■ | Ct 2251 10 mg/kg |
| | ▨ | vehicle control | ▤ | Dex 5 mg/kg |
| | ■ | DHEAS | ▨ | normal ears |
| | ▦ | DHEAS and Ct 2251 10 mg/kg | | | results given as mean±sem.
*=p<0.05 vs DHEAS, *=p<0.05 vs CT2251
$=p<0.05 vs vehicle control FIG. 11 shows a histogram analysis of the effect of Ct 2251 on Delayed Type Hypersensitivity

Figure 12:
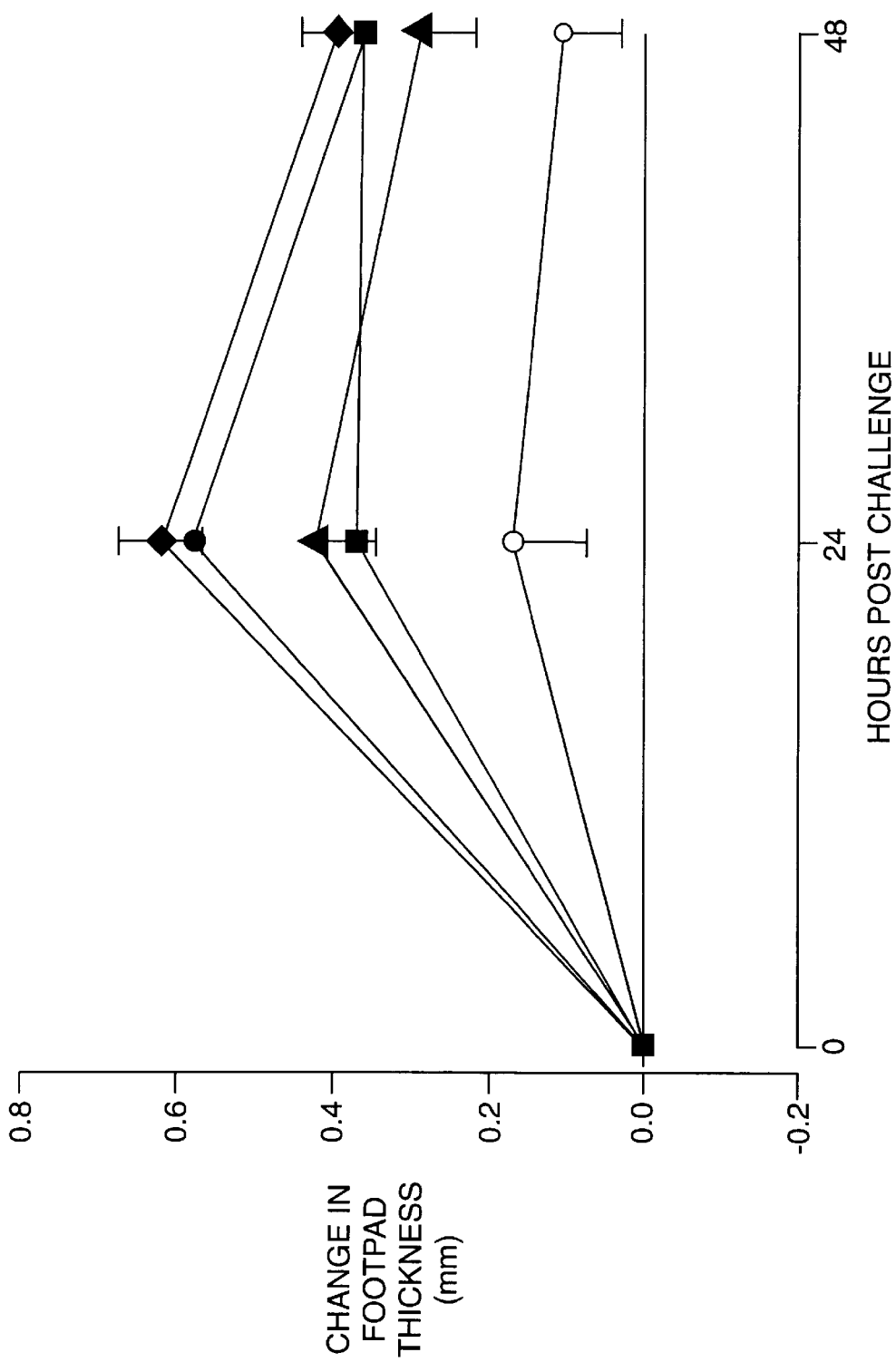

| | | |
|---|---|---|
| A | ■ | DHEA 5 mg/kg |
| | □ | DHEAS 5 mg/kg |
| | ■ | DEXA 5 mg/kg |
| | ▨ | DHEA 5 mg/kg and Ct 2251 10 mg/kg |
| | ▧ | DHEA 5 mg/kg and Ct 2251 0.1 mg/kg |
| | ▦ | Ct 2251 10 mg/kg |
| | ▤ | Ct 2251 0.1 mg/kg |
| B | ■ | DHEA 5 mg/kg |
| | □ | DHEAS 5 mg/kg |
| | ■ | DEXA 5 mg/kg |
| | ▨ | DHEAS 5 mg/kg and Ct 2251 10 mg/kg |
| | ▧ | DHEAS 5 mg/kg and Ct 2251 0.1 mg/kg |
| | ▦ | Ct 2251 10 mg/kg |
| | ▤ | Ct 2251 0.1 mg/kg | steroids given on day 0 and 3 subcutaneously. Response at 24 h post challenge.
Results given as mean±sem, n=7–8
$, *p<0.05 ANOVA FIG. 12 shows a graph of the effect of Ct 2251 on DTH in rats. CT 2251 given on days 0, 3 and 4 subcutaneously

| | | | |
|---|---|---|---|
| ○ | challenge only | ■ | Ct 2251 1 mg/kg |
| ● | vehicle control | ● | Ct 2251 0.1 mg/kg |
| ▲ | Ct 2251 10 mg/kg | | | results given as mean±sem, n=6–7

Figure 13:
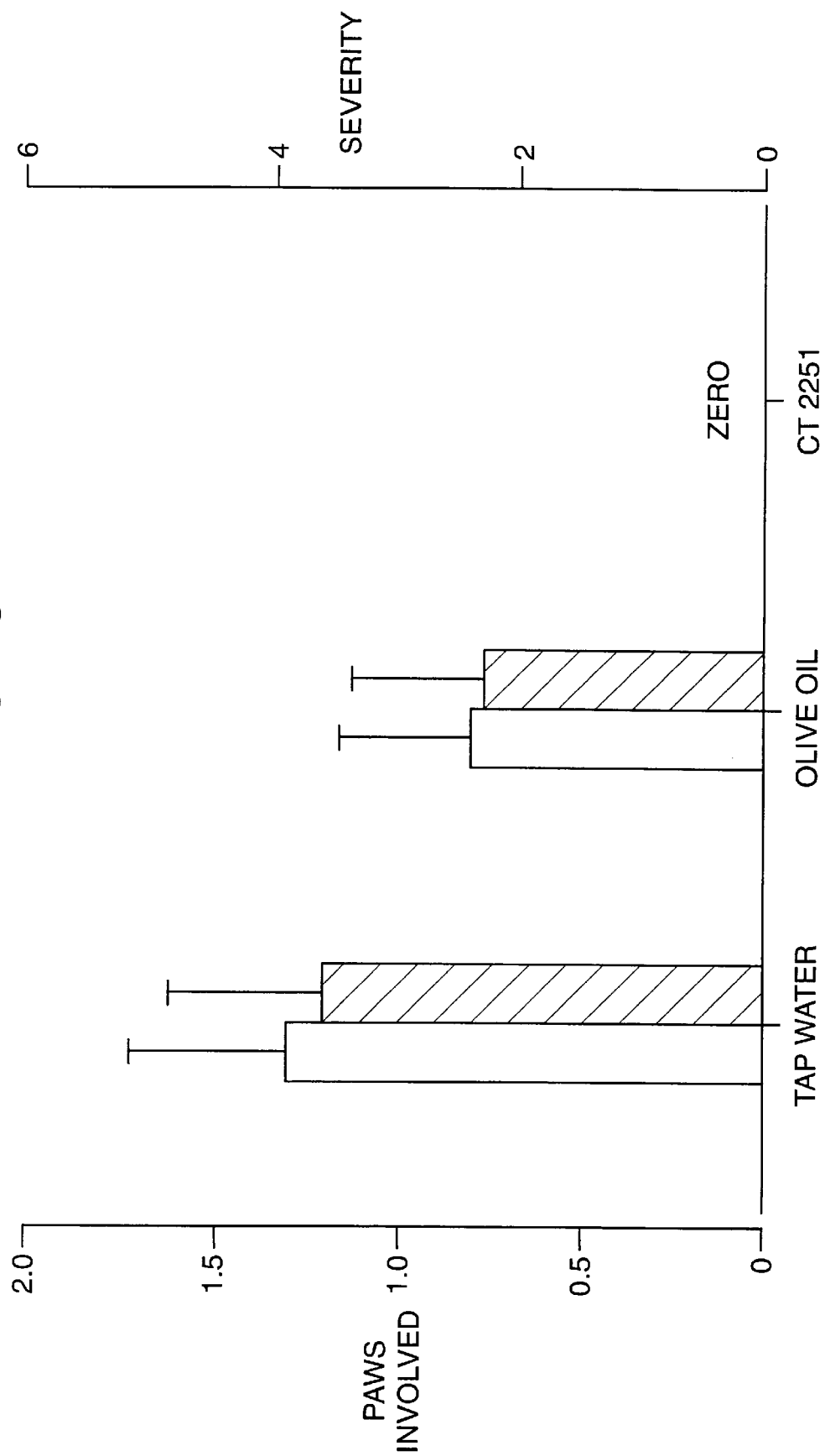

FIG. 13 shows effect of Ct 2251 on collagen induced arthritis in mice

| | |
|---|---|
| □ | paws involved |
| ▨ | severity | data are mean±sem, n=10. Incidence of arthritis was 60% and 40% in tap water and olive oil groups respectively.

FIG. 14 shows
A the effect of Ct 2251 and DHEAS on carrageenan pleurisy —exudate
DEX 1 mg/kg, Ct2251 10 mg/kg, DHEAS 5 mg/kg
B the effect of Ct 2251 and DHEAS on carageenan pleurisy —Total Cells
DEX 1 mg/kg, Ct 2251 10 mg/kg, DHEAS 5 mg/kg
Results given as mean±sem. *=sig. diff vs control by ANOVA.

Figure 15:
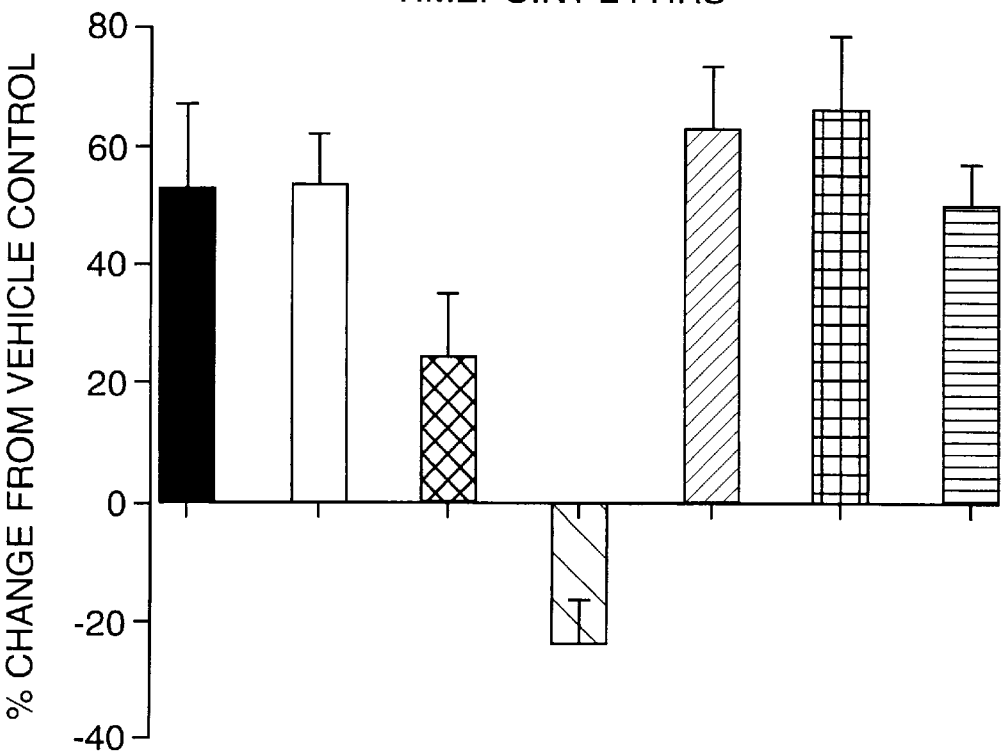

FIG. 15 shows a histogram analysis of contact sensitisation results

| | |
|---|---|
| ■ | DHEA (5 mg/kg) |
| □ | DHEA (0.5 mg/kg) |
| ■ | DHEA (0.05 mg/kg) |
| ▨ | DHEA (0.005 mg/kg) |
| ▧ | AED (5 mg/kg) |
| ▦ | AED (0.5 mg/kg) |
| ▤ | AED (0.05 mg/kg) |

Sensitised with 2.5% oxazalone, challenged with 0.25%.
Steroids given on day 0 and 4 subcutaneously, 20% dmso: 80% olive oil.
Results given as mean±sem, n=10.

Figure 16:
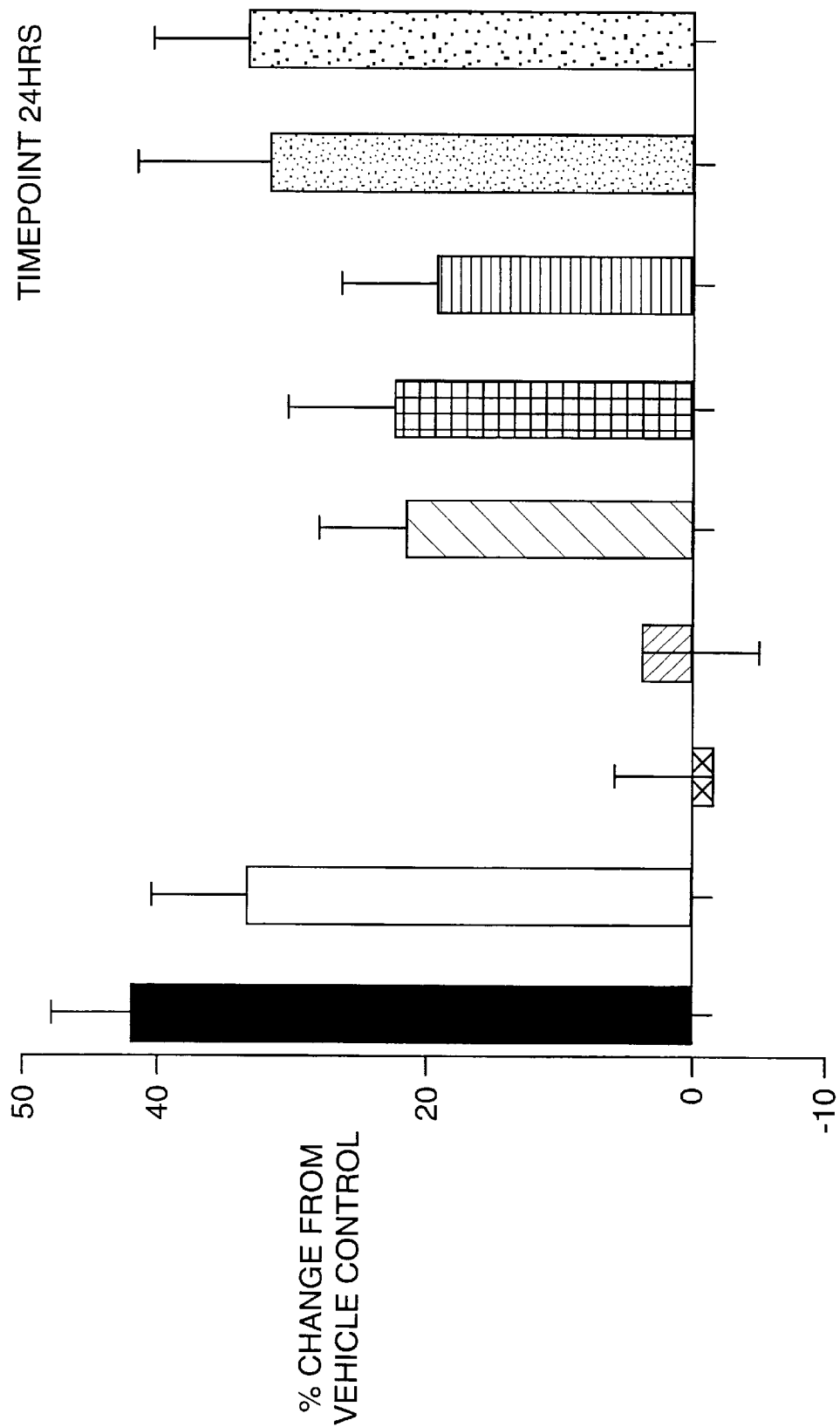

FIG. 16 shows a histogram analysis of contact sensitisation results

| | |
|---|---|
| ■ | DHEAS (5 mg/kg) |
| □ | DHEAS (0.5 mg/kg) |

-continued

| | |
|---|---|
| ■ | DHEAS (0.05 mg/kg) |
| ▨ | DHEAS (0.005 mg/kg) |
| ▨ | AEDS (5 mg/kg) |
| ▨ | AEDS (0.5 mg/kg) |
| ▤ | AEDS (0.05 mg/kg) |
| ▨ | AEDS (0.005 mg/kg) |
| ▦ | AEDS (0.0005 mg/kg) |

Sensitised with 2.5% oxazalone, challenged with 0.25%.
Steroids given on day 0 and 4 subcutaneously, 20% dmso: 80% olive oil.
Results given as mean±sem, n=10.

Figure 17:
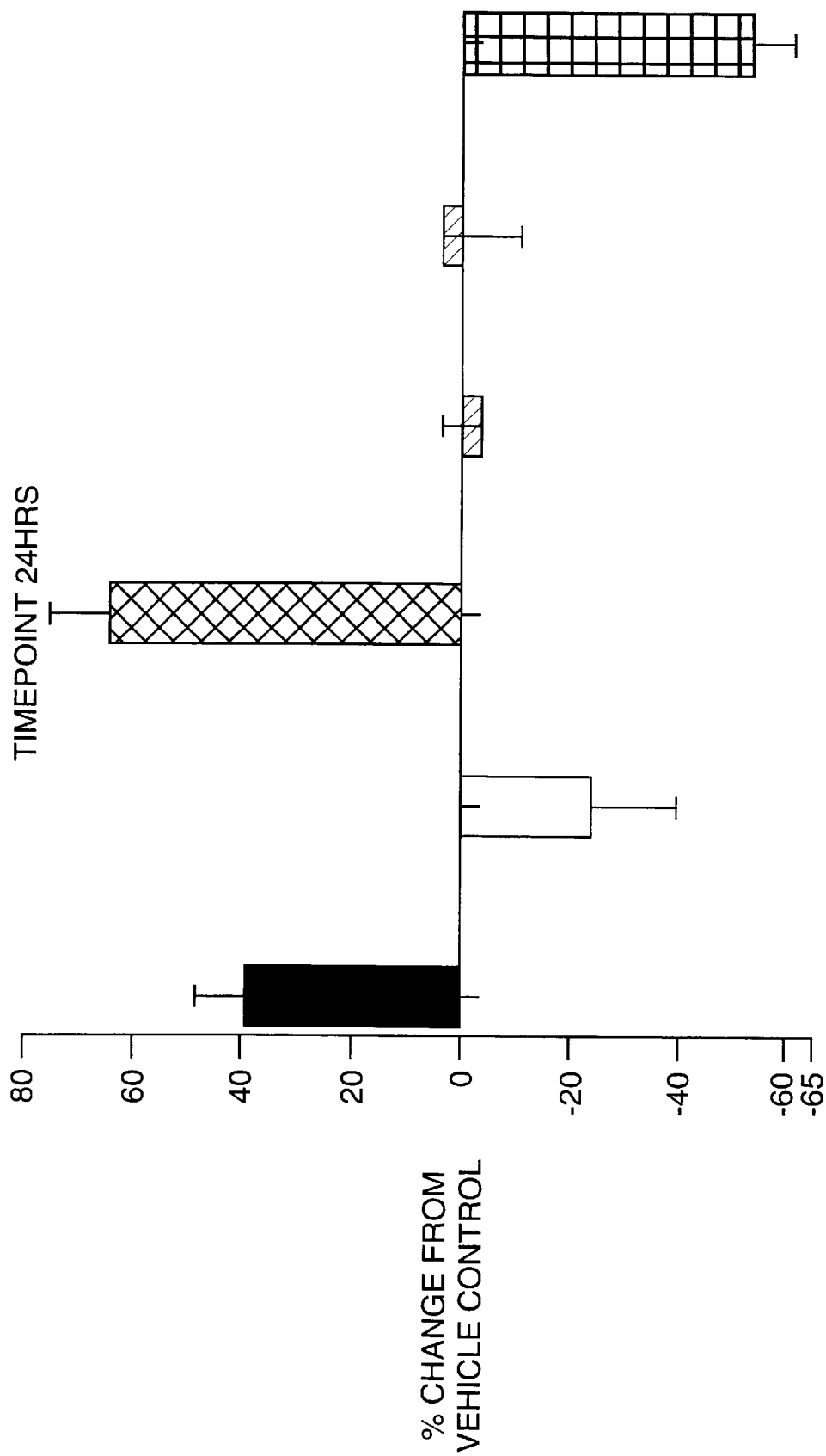

FIG. 17 shows a histogram analysis of contact sensitisation results

| | |
|---|---|
| ■ | AEDS (5 mg/kg) |
| ☐ | (5 mg/kg) and CT 2251 (0.1 mg/kg) |
| ■ | DHEAS (5 mg/kg) |
| ▨ | DHEAS (5 mg/kg) and CT 2251 (0.1 mg/kg) |
| ▨ | CT 2251 (0.1 mg/kg) |
| ▦ | DEX (5 mg/kg) |

Sensitised with 2.5% oxazalone, challenged with 0.25%.
Steroids given on day 0 and 4 subcutaneously, 20% dmso: 80% olive oil.
Results given as mean±sem, n=10–11.

Figure 18:
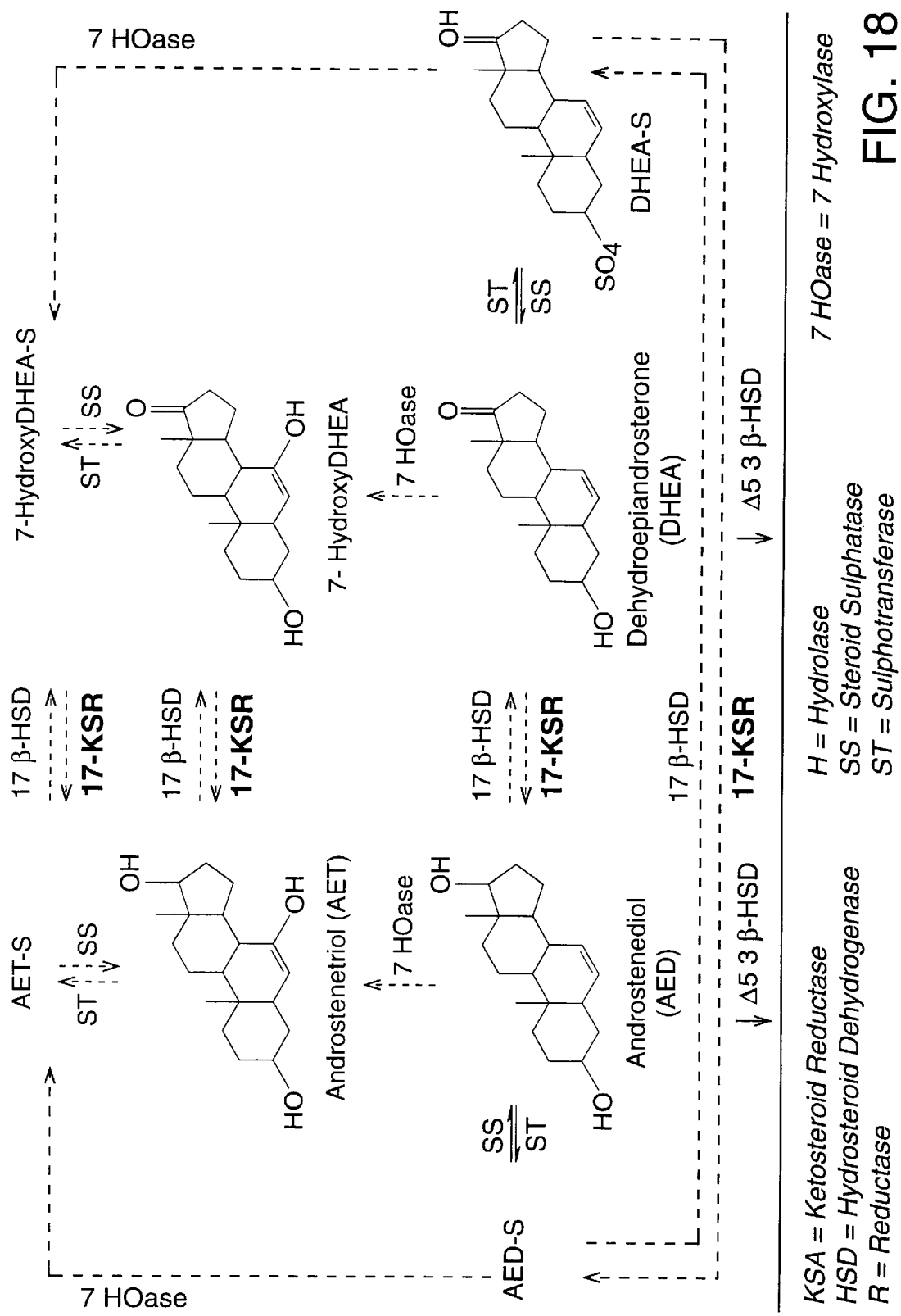

FIG. 18 shows a diagram of the pathways of DHEA metabolism.

DESCRIPTION OF SPECIFIC EMBODIMENTS OF THE INVENTION EXAMPLES

Enzyme Assays
1. Identification of Potent Steroid Sulphatase Inhibitors

PROTOCOL FOR DHEAS SULPHATASE ASSAY

Methods
a) Human placental microsomal steroid sulphatase

ENZYME: Human placental microsomes prepared as described in (Santner, S. J., et al (1984) J. Clin. Endocrinol. Metab. 59 29).

ASSAY: All assays were carried out in (at least) duplicate. The reaction mixture consisted of either PBS+250 mM sucrose (placental microsomes), containing 1 $\mu$mol/l DHEAS [concentration chosen because approx. 10°<Km (app)] with 0.05% (v/v) [$^3$H] substrate and 0.05% (v/v) [$^{14}$C] DHEA) in 0.5% (v/v DMSO. The reaction was initiated by addition of appropriately diluted) such that 10% substrate conversion occurred during the assay) enzyme and incubated for 30 min at 30° C. Reactions were stopped by addition of 1000 $\mu$l toluene to the reaction mixture, vortexed (2*40 sec on max setting of multitube vortexer), then allow to settle for 5 min. 500 $\mu$l top (solvent) layer removed to scintillation vial. add 10 ml scintillation fluid (Ultima Gold XR) then counted for radioactivity on a scintillation counter. As controls, enzyme was excluded from some reaction mixtures and 50% solvent and aqueous layers removed and counted for radioactivity in order to determine background (in solvent layer) and total (in aqueous layer) [$^3$H]. [$^{14}$C] DHEA is included to enable back correction to allow for product (DHEA) recovery (normally >98%).

EFFECT OF INHIBITORS: Inhibitors were included in the above reaction at varying concentrations in 0.5% (v/v) DMSO [or 5% (v/v) DMSO if necessary due to poor solubility of inhibitor] bringing the final DMSO concentration in the assay to 1% (v/v) [or 5.5% (v/v)].

The enzyme would be assayed for estrone sulphate sulphatase activity similarly except with ES in the assay instead of DHEAS.

b) Recombinant steroid sulphatase (as Stein et al J. Biol. Chem. 264, 13865–13872, 1990; Yen et al Cell, 49, 443–454, 1987).

ENZYME: human recombinant placental steroid sulphatase (expressed in NSO cells). Either crude extracts, partially pure or pure enzyme may be used. The enzyme will be assayed as described for human placental steroid sulphatase as described above, except the assay buffer will be 50 mM Tris/HCl of appropriate pH (~7.5), containing 0.1% (v/v Triton×100.

Calculations
1. Of rate of reaction of steroid sulphate sulphatase.

3H/14C dpm ratioed for all samples including controls i.e. (ratioed 3H dpm bottom layer "no enzyme" controls to 14C top layer "no enzyme controls" to give total 3H/14C).

3H/14C "no enzyme" controls (background) were subtracted from 3H/14C samples (not total) to give net 3H/14C values.

Net 3H/14C values were divided by total, then result multiplied by substrate concentration (1 $\mu$mol/l) to give concentration of product.

Concentration of product was divided by time of incubation (30 min) to give rate (V) substrate conversion (in $\mu$mol/l/min).

2. % inhibition in the presence of inhibitor.

[1−((rate+inhibitor)/(rate−inhibitor))]×100=% inhibition. where rate+inhibitor =rate in the presence of inhibitor and where rate−inhibitor=rate in the absence of inhibitor

3. IC50

The computer program MULTICALC (Pharmacia) was used to fit a 4 parameter, unweighted curve to % inhibition (y axis) vs log (concentration of inhibitor) (x axis) and to determine the concentration of inhibitor which reduces the enzyme activity (in the absence of inhibitor) by 50% (IC50) from the graph.

4. $K_m$ (app) and $K_i$ (app)

The enzyme activity would be determined at a variety of substrate concentrations then $K'_m$ calculated from these data using the computer program Enzfitter (Leatherbarrow R. A. (1987) Enzfitter; a non-linear regression data analysis programme for the IBM PC. Elsevier Biosoft, Cambridge U.K.). This would be repeated at a variety of inhibitor concentrations and $K_i$ determined from the $K'_m$ values obtained according to the equation:

$K_m' = K_m(1+[I]K_i)$ where $K_m' = K_m$ in presence of inhibitor at concentration [I].

The median $K_i$ would be taken as a representative figure.

c) DHEAS sulphatase activity in U937 cell extracts.

Method

The inhibitors Ct 2211 and Ct 2251 were dissolved in 100% ethanol and 100% dimethyl sulphoxide (DMSO) respectively at stock concentrations of 20 mM. These were titrated in their respective solvents over a range of assay concentrations. The tritiated substrates DHEA sulphate and estrone sulphate were obtained from New England Nuclear and diluted in ethanol to give a final concentration of 70 nM for use in the assay. U937 cells were grown in RPLI containing 10% foetal bovine serum and harvested at a cell concentration of 1×10$^6$/ml. These were washed in serum free medium stored at −70° C. at 1×10$^8$/ml in Tris buffered saline pH7.4+1% triton X-100 and sonicated prior to use in the assay.

50 μl of substrate in ethanol was added to each assay tube and the solvent removed in a rotary vacuum evaporator. For Ct 2211 dissolved in ethanol. 25 μl of each dilution was added to an assay tube and the solvent again removed by evaporation. With Ct 2251 dissolved in DMSO, 25 μl of U937 cells sonicate, diluted to a cell equivalent of 1.25× 10$^7$/ml, was added to each tube. With Ct 2251 225 μl of U937 cell solicate was added to each tube giving a final concentration of 10% DMSO. The tubes were incubated at 37° C. for 4 hours and the reaction stopped with methanol. After centrifugation scintillation fluid was added to extract the desulphated substrate and the CPM present in an aliquot of the organic phase were counted using a beta counter.

Figure 1:
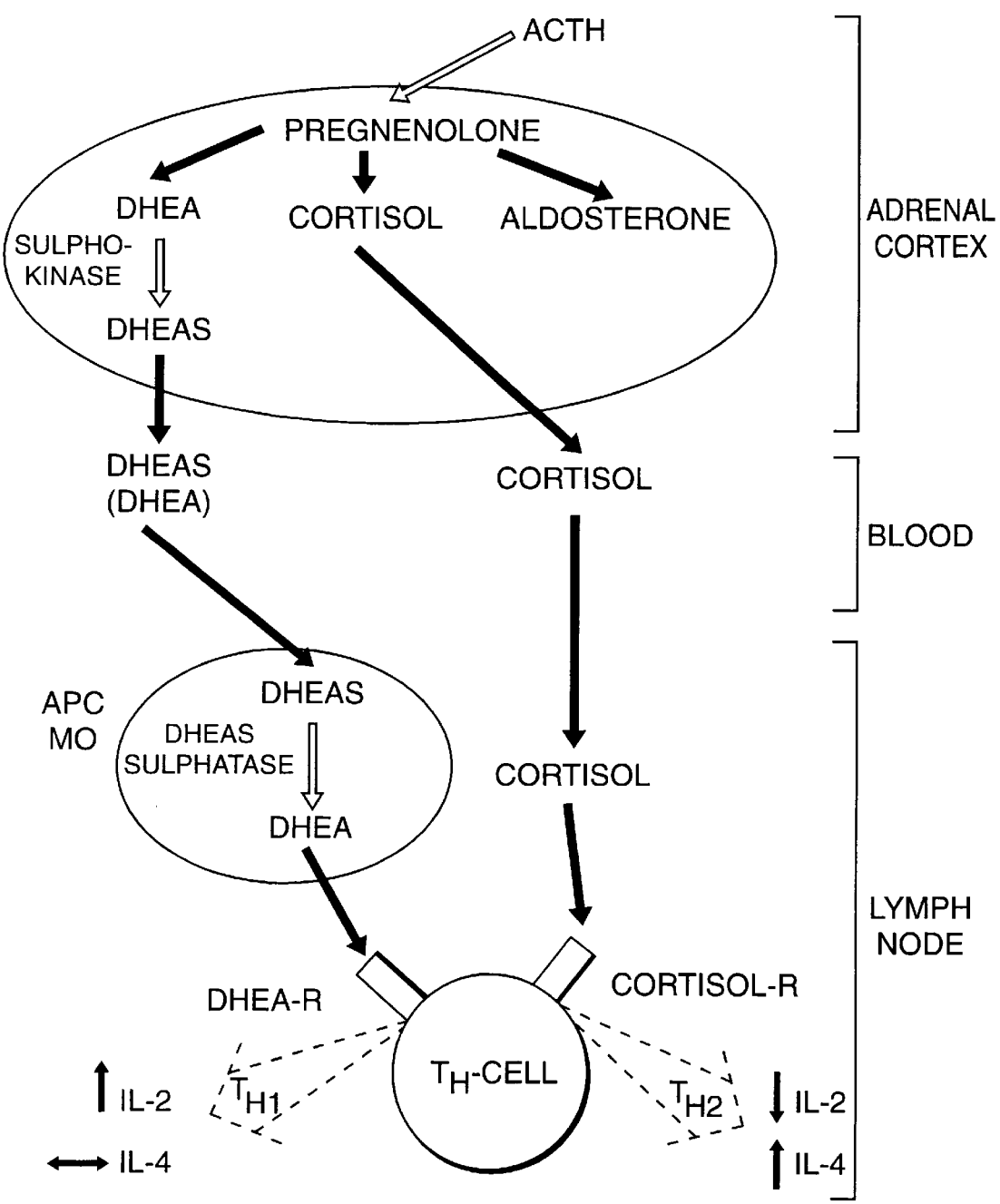
FIG. 1 shows a schematic representation of the influence of adrenal steroids on $T_H$ cell cytokine production.
Figure 2:
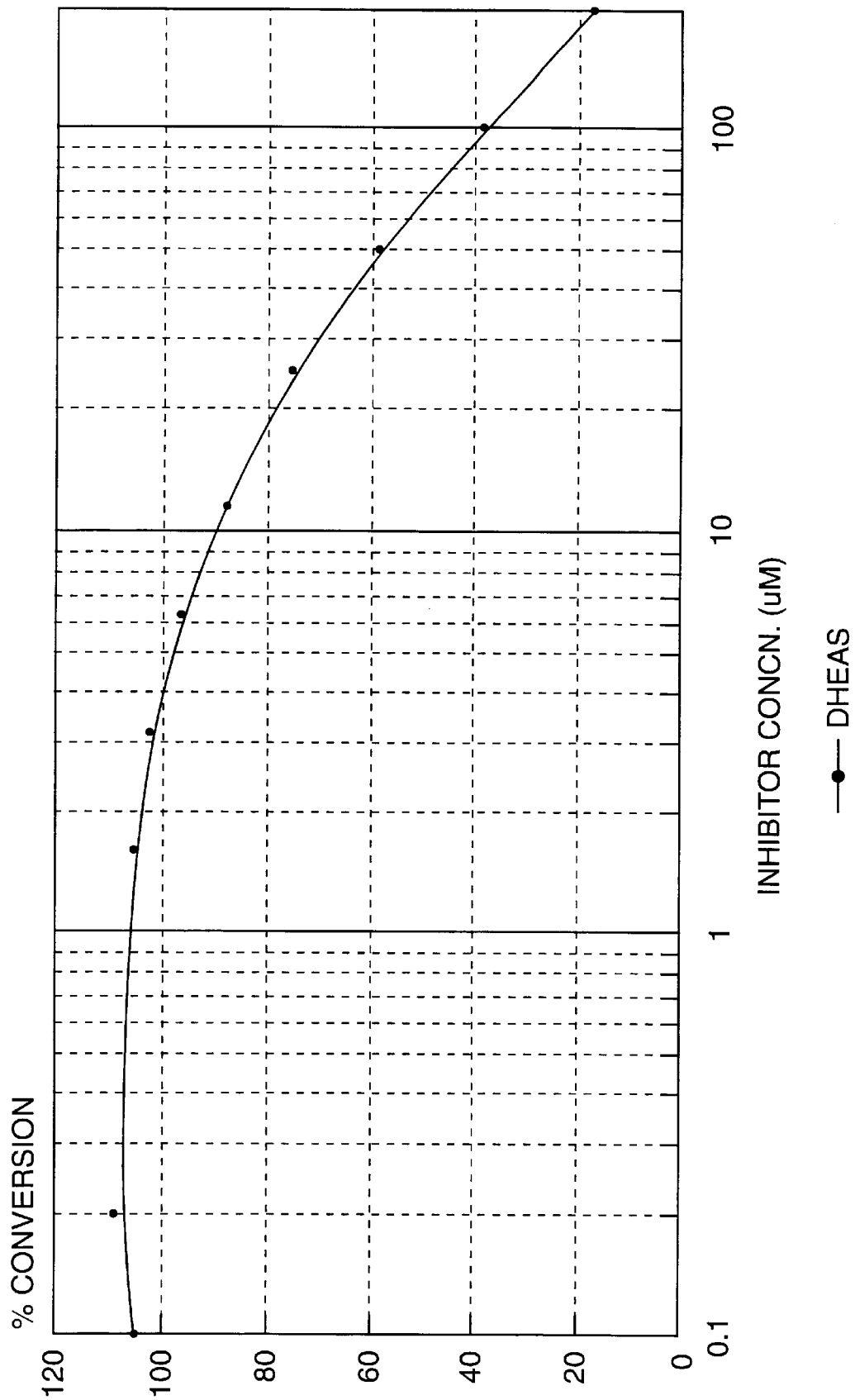
FIG. 2 shows a graphic representation of CT2211 inhibition of DHEAS conversion by U937 sulphatase.
Figure 3:
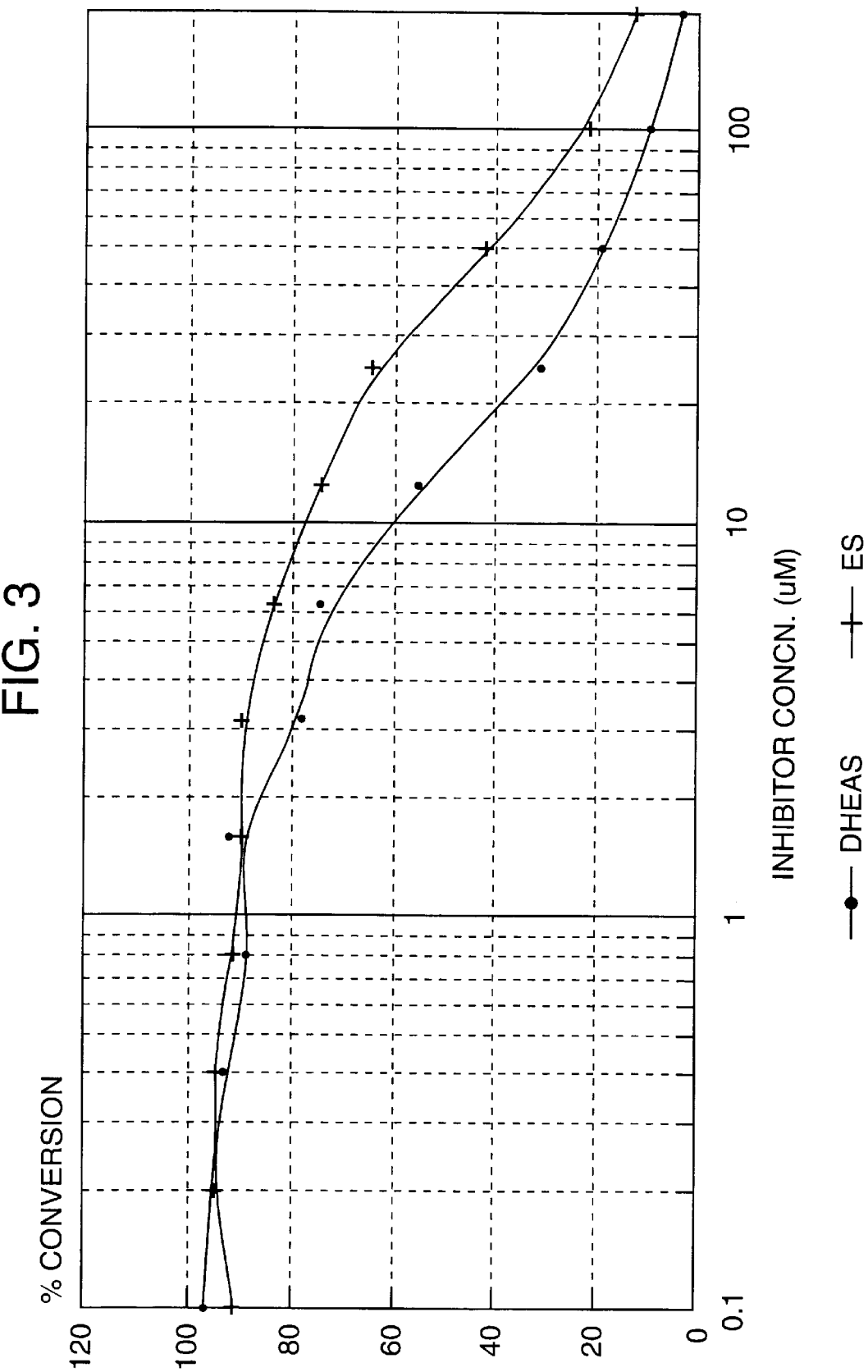
FIG. 3 shows a graphic representation of CT2251 inhibition of DHEAS and ES conversion by U937 sulphatase.

FIG. 2 shows the ability of Ct 2211 to inhibit the sulphatase derived from U937 cells using DHEAS as a substrate. FIG. 3 shows the ability of Ct 2251 to inhibit the same enzyme using both DHEAS and estrone sulphate as substrates.

Total CPM

In order to obtain total counts 10 μl of the aqueous fraction of the duplicate tubes containing only hot DHEA-s were counted after addition of scintillant and the total cpm calculated as follows:

$$\text{total cpm} = \frac{500}{10} \times \text{cpm for 10 } \mu l$$

Proportions of DHEA-s converted to DHEA =

$$\frac{\text{cpm-backgroundcpm}}{\text{total cpm}} = P$$

uMoles DHEA formed in 4 hours =

$$P \times \text{total no. uMoles per tube} = M$$

$$v_0 = M / \text{time in minutes}$$

Total [Substrate] = uMolar cold + uMolar hot $$\% \text{ inhibition} = \left[1 - \left(\frac{v_0 + \text{inhibitor}}{v_0 - \text{inhibitor}}\right)\right] \times 100$$

where $v_o$+inhibitor-rate in the presence of inhibitor and $v_o$-inhibitor=rate in the absence of inhibitor.

IC$_{50}$ determined as described previously.

d) Other, as yet unknown DHEAS sulphatase activities will be assayed broadly as described above using a suitable buffer (i.e. one in which the enzyme has measurable activity).

2. Selectivity of Potent Steroid Sulphatase Inhibitors for Steroid Sulphatase only The effect of steroid sulphatase inhibitors would be examined on other related sulphatase activities i.e. aryl sulphatases A and B.

The effects of steroid sulphatases directly on enzymes/receptors of the glucocorticoid pathway would be examined.

The effects of steroid sulphatase inhibitors on glucose-6-phosphate dehydrogenase would be examined.

Effects on these enzymes/receptors would be considered detrimental and to be avoided as far as possible.

3. Identification of Inhibitors of DHEAS and Related Sulphated Steroids Uptake into Cells An assay to identify such inhibitors would measure uptake of [3H]DHEAS or a related sulphated steroid into an appropriate cell line and the effects of inhibitors on such an uptake. This is described for [$^3$H] DHEAS but it will be apparent to one skilled in the art that this could be modified using standard techniques for identifying inhibitors of uptake of related sulphated steroids.

1. An appropriate cell line (i.e. one which takes up [$^3$H] DHEAS above background levels) would be incubated with 1 μM DHEAS containing 1% (v/v) [$^3$H] DHEAS at 37° C. for a given time (>1 h) in a serum free cell culture medium (RPMI)±various inhibitor concentrations.
2. At the end of that time cells would be harvested (if adherent, first trypsinised off cell culture plate) by centrifugation, washed 3 times in excess (10 ml) of the serum free cell culture medium and counted for radioactivity in a scintillation counter (all cells lysing in scintillation fluid).
3. Calculation
   1. Net [$^3$H] DHEAS uptake
      [$^3$H] in cells—[$^3$H] in a suitable cell line known not to take up DHEAS (e.g. U937), i.e. background.
      =net [$^3$H] uptake.
   2. % Inhibition $$\% \text{ inhibition} = \left[1 - \left(\frac{\text{net [}^3H\text{] uptake + inhibitor}}{\text{net [}^3H\text{] uptake - inhibitor}}\right)\right] \times 100$$

where net [$^3$H] uptake+inhibitor=uptake in the presence of inhibitor and net [$^3$H] uptake-inhibitor=uptake in the absence of inhibitor.

3. IC$_{50}$ Values
   —determined as described for inhibition of sulphatase activity.

Results obtained to date:
1. vs U937 DHEAS sulphatase activity

| CT No. | Apparent IC50 (μM) |
|--------|--------------------|
| 2211   | 84                 |
| 2251   | 0.04               |

2. vs human placental microsomal DHEAS sulphatase activity

| CT No. | Apparent IC50 (μM) |
|--------|--------------------|
| 2211   | 152                |
| 2251   | 0.005              |

2. IN VITRO CELL IMMUNOLOGY IMMUNE FUNCTION

Ex vivo T cell function experiments are performed where an interaction between MHC-II and the T cell receptor is an obligatory requirement for T cell activation. Steroid sulphate sulphatase inhibitors are tested in mixed lymphocyte reactions, which measure both naive and memory T cell activation, and recall responses to tetanus toxoid and to housedust mite which measure memory T cell responses of Th1+Th2 type respectively.

The principle of the experiment is that when leucocytes from one individual are mixed with those of another who expresses different HLA alleles, they will recognise each other as foreign and the lymphocytes will become activated. This activation is dependent, primarily, on interactions between the CD3/TcR complex on T cells and the MHC-II molecule on antigen presenting cells. Antibodies that bind to MHC-II are known to inhibit this reaction.

Leucocytes are prepared fresh for each experiment. Human venous blood from two individuals is drawn into endotoxin free tubes containing heparin. Peripheral blood mononuclear cells (PBMC) are prepared by density gradient centrifugation according to the manufacturers instructions (Pharmacia). PBMC are adjusted to $2 \times 10^6$ cells/ml in RPMI 1640 medium (Gibco UK) containing 2 mM Glutamine (Gibco UK), 100 $\mu$/ml/100 $\mu$g/ml Penicillin/Streptomycin (Gibco) and 10% foetal calf serum (Sigma UK), in which all manipulations, dilutions and incubations are done. PBMC from one individual are irradiated with 3000 rads. These cells will be stimulate a response from the other individual.

Serial inhibitor dilutions are prepared in triplicate in sterile U-bottom 96 well microtitre plates (Falcon UK) in 100 $\mu$l. Control wells containing medium only and optimal Cyclosporin (Sandimmun, Sandoz) levels (100 nM) are also prepared to establish the maximum response and maximum inhibition, respectively. Equal numbers of irradiated stimulators and responders are mixed together and 100 $\mu$l are added to each well±DHEA-s added in 10 $\mu$l. Wells of stimulator alone and responders alone are also set up as controls. The experiment is incubated at 37° C. in 100% humidity and 5% $CO_2$ for 5 days. Response is measured by assessing proliferation during the last 18 hours of culture by incubation with 1 $\mu$Ci/well $^3$H-Thymidine (Amersham UK), harvesting on to glass filter mattes and counting using a beta counter.

Results are plotted as CPM against inhibitor concentration.

Supernatants are removed and assayed for cytokine production IL-2, IFN$\gamma$, TNF and LT.

T-CELL RECALL RESPONSE TO TETANUS TOXOID

The principle of the experiment is that T lymphocytes from an individual previously immunised with Tetanus Toxoid (TT) will respond to TT when re-exposed ex vivo. This activation is dependent on the interaction between the CD3/TcR complex on T cells and the MHC-II molecule on cells which process and present the antigen. Antibodies that bind to MHC-II are known to inhibit this reaction.

Lymphocytes are prepared fresh for each experiment. Human venous blood is drawn into endotoxin free tubes containing heparin. Peripheral blood mononuclear cells (PBMC) are prepared by density gradient centrifugation according to the manufacturers instructions (Pharmacia), PBMC are adjusted to $2 \times 10^6$ cells/ml in RPMI 1640 medium (Gibco UK) containing 2 mM Glutamine (Gibco UK), 100 $\mu$/ml/100 $\mu$g/ml Penicillin/Streptomycin (Gibco) and 10% foetal calf serum (Sigma UK), in which all manipulations, dilutions and incubations are done.

Serial inhibitor dilutions are prepared in triplicate in sterile U-bottom 96 well microtitre plates (Falcon UK) in 100 $\mu$l. 50 $\mu$l containing an optimal concentration of TT, previously determined by experimentation, is added to all wells. Control wells containing medium only or Cyclosporin (Sandimmun, Sandoz) (100 nM) are also prepared to establish the maximum response and maximum inhibition, respectively. 50 $\mu$l PBMC are then added to each well±DHEA-s added in 10 $\mu$l. The experiment is incubated at 37° C. in 100% humidity and 5% $CO_2$ for 7 days. Response is measured by assessing proliferation during the last 18 hours of culture by incubation with 1 $\mu$Ci/well $^3$H-Thymidine, harvesting on to glass filter mattes and counting using a beta counter.

Results are plotted as CPM against inhibitor concentration.

Supernatants are also removed and tested for cytokine production IL-2, IL-4, IL-5, TNF, LT, IFN$\gamma$.

T CELL RECALL RESPONSE TO HOUSE DUST MITE

The principle of the experiment is that T lymphocytes from an atopic individual known to be allergic to house dust mite will respond to extracts of house dust mite when re-exposed ex vivo. This activation is dependent on the interaction between the CD3/TcR complex on T cells and the MHC-II molecule on cells which process and present the antigen.

Lymphocytes are prepared fresh for each experiment. Human venous blood is drawn into endotoxin free tubes containing heparin. Peripheral blood mononuclear cells (PBMC) are prepared by density gradient centrifugation according to the manufacturers instructions (Pharmacia). PBMC are adjusted to $2 \times 10^6$ cells/ml in RPMI 1640 medium (Gibco UK) containing 2 mM Glutamine (Gibco UK), 100 $\mu$/ml/100 $\mu$g/ml Penicillin/Streptomycin (Gibco) and 10% foetal calf serum (Sigma UK), in which all manipulations dilutions and incubations are done.

Serial inhibitor dilutions are prepared in triplicate in sterile U-bottom 96 well microtitre plates (Falcon UK) in 100 $\mu$l. 50 $\mu$l containing an optimal concentration of HDM, previously determined by experimentation, is added to all wells. Control wells containing medium only or Cyclosporin (Sandimmun, Sandoz) (100 nM) are also prepared to establish the maximum response and maximum inhibition, respectively. 50 $\mu$l PBMC are then added to each well±DHEA-s. The experiment is incubated at 37° C. in 100% humidity and 5% $CO_2$ for 7 days. Response is measured by assessing proliferation during the last 18 hours of culture by incubation with 1 $\mu$Ci/well $^3$H-Thymidine, harvesting on to glass filter mattes and counting using a beta counter.

Supernatants are also removed and tested for IL-2, IL-4, IL-5, IFN$\gamma$, TNF and LT.

Results are plotted as CPM against inhibitor concentration.

IMMUNE FUNCTION

Ex Vivo T cell function experiments are performed where an interaction between MHC-II and the T cell receptor is not an obligatory requirement for T cell activation.

The mitogens PHA, Superantigens and OKT3 are used.

When mixed with the lectin PHA staphylococcal enterotoxins, or the anti- CD3 Ab OKT3, T cells will respond by becoming activated, proliferating and secreting cytokines.

Lymphocytes are prepared fresh for each experiment. Human venous blood is drawn into endotoxin free tubes containing heparin. Peripheral blood mononuclear cells (PBMC) are prepared by density gradient centrifugation according to the manufacturers instructions (Pharmacia). PBMC are adjusted to $2 \times 10^6$ cells/ml in RPMI 1640 medium (Gibco UK) containing 2 mM Glutamine (Gibco UK), 100 $\mu$/ml/100 $\mu$g/ml Penicillin/Streptomycin (Gibco) and 10% foetal calf serum (Sigma UK), in which all manipulations, dilutions and incubations are done.

Serial inhibitor dilutions are prepared in triplicate in sterile U-bottom 96 well microtitre plates (Falcon UK) in 100 $\mu$l. 50 $\mu$l containing an optimal concentrations of mutogens, previously determined by experimentation, are added to all wells. Control wells containing medium only or Cyclosporin (Sandimmun, Sandoz) (100 nM) are also prepared to establish the maximum response and maximum inhibition, respectively, 50 µl PBMC are then added to each well±DHEA-s in 10 µl. The experiment is incubated at 37° C. in 100% humidity and 5% $CO_2$ for 7 days. Response is measured by assessing proliferation during the last 18 hours of culture by incubation with 1 µCi/well $^3$H-Thymidine, harvesting on to glass filter mattes and counting using a beta counter.

Results are plotted as CPM against inhibitor concentration.

Supernatants are removed for cytokine assay IL-2, 4, 5, LT, TNF, IFNγ and IL-1.

3. IN VIVO PHARMACOLOGY FOR DHEAS SULPHATASE, INHIBITORS

The effect of DHEA, DHEAS and their inhibitors have been tested in 2 models of immune function in mice.

1. Contact Sensitisation (CS)

On day 0, mice were painted on their shaved right flank with 50 µl 2.5% oxazalone or vehicle (acetone 4:1 olive oil). On day 5 animals were challenged on their dorsal right ear surface with 25 µl of either 0.75% or 0.25% oxazalone. Prior to ear challenge, and 24, 48 and 72 hour post challenge ear thickness was measured using an engineer's micrometers. Ear swelling is determined as the difference in thickness prior and post challenge. The data are expressed as percentage change from the vehicle treated groups given sensitisation and challenge.

2. Delayed Type Hypersensitivity (DTH)

On day 0, animals were injected intravenously with $10^6$ washed SRBC in 0.1 ml saline. Four days later animals were challenged in the right hind footpad with $10^6$ washed SRBC in 50 µl saline. Footpad thickness is measured prior to challenge, 24, 48 and 72 hours post challenge using calipers. Footpad swelling is determined as the difference in thickness prior and post challenge. The data are expressed as percentage change from the vehicle treated groups given sensitisation and challenge.

Steroids and Inhibitors

DHEA, DHEAS were administered at various times, generally at time of sensitisation (day 0) and time of challenge (day 3 or 4-DTH model, day 4 or 5-(CS-model) in order to obtain an augmentation of the immune response above non-steroid treated animals.

Different doses of the inhibitors have been used, and compared to the effect of dexamethasone as potential immunosuppressive/anti-inflammatory agents.

EXAMPLE 1

In vivo Assay of Steroid Sulphate Sulphatase Inhibitors

Three inhibitors of steroid sulphate sulphatase prepared as described in Howarth et al J. Med. Chem. (1994) 37, 219–221 and Howarth et al (1993) Bioorganic & Medicinal Chemistry Letters 3 (2) 313–318 have been tested for their immunosuppressive ability in a mouse contact sensitisation model. The basic protocol is outlined above. Two separated experiments have been performed.

The inhibitors tested were:
CT 2210: Estrone-3-0-(N,N-dimethyl)sulphamate
CT 2211: Estrone 3-methylphosphonate
CT 2251: Estrone 3-0-sulphamate

CONTACT SENSITISATION

Experiment 1

Animals were sensitised with 2.5% oxazolone on day 0 and ear challenged with 0.25% oxazalone on day 5. Steroids (DHEA, DHEAS, dexamethasone and inhibitors CT 2210 and CT 2211) were given on days 0, 4 and 5 as subcutaneous injections dissolved in olive oil. The data are presented as percentage change from the vehicle treated group given sensitisation and challenge (positive control). Animals were randomised into 10 treatment groups (n=7–8 per group).

| Group 1: | sensitisation and challenge plus olive oil (positive control) |
|---|---|
| Group 2: | sensitisation and challenge plus DHEA 100 µg/mouse |
| Group 3: | sensitisation and challenge plus DHEAS 100 µg/mouse |
| Group 4: | sensitisation and challenge plus dexamethasone 100 µg/mouse |
| Group 5: | sensitisation and challenge plus DHEA 100 µg/mouse + CT 2210 2 mg/mouse |
| Group 6: | sensitisation and challenge plus DHEA 100 µg/mouse + CT 2211 2 mg/mouse |
| Group 7: | sensitisation and challenge plus DHEAS 100 µg/mouse + CT 2210 2 mg/mouse |
| Group 8: | sensitisation and challenge plus DHEAS 100 µg/mouse + CT 2211 2 mg/mouse |
| Groups 9/10 | sensitisation and challenge plus CT2210 or CT2211 2 mg/mouse |

Figure 4:
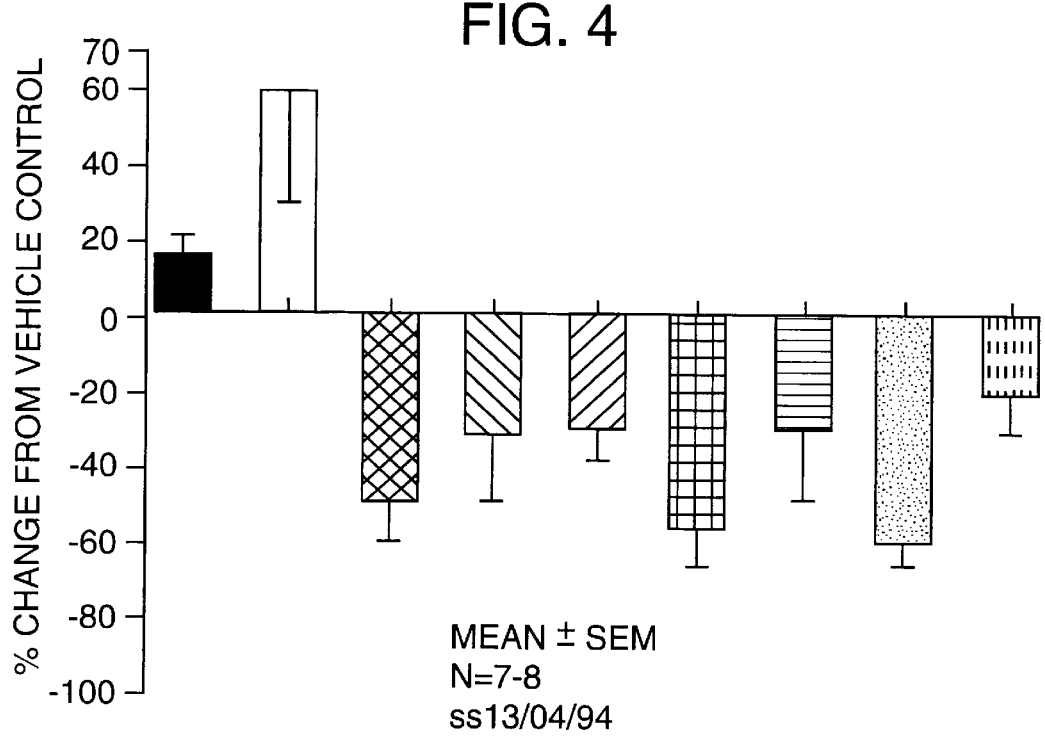
FIG. 4 shows a histogram analysis of contact sensitisation results.

The data are shown in FIG. 4 measured at 48 post challenge. Both DHEA and DHEAS alone augmented the normal increase in ear thickness seen with the procedure indicating an immunostimulatory effect. Dexamethasone reduced the response indicating an immunosuppressive (or anti-inflammatory) effect. Both CT2210 and CT2211 were able to reverse the stimulatory effects of either DHEA and DHEAS and furthermore were able to attenuate the ear swelling seen in the absence of DHEA and DHEAS. These data indicate that CT2210 and 2211 both inhibitors of steroid sulphate sulphatase, are immunosuppressive in this model.

EXPERIMENT 2

Effect of DHEA, DHEAS and Dexamethasone (DEX)

Animals were randomised into 5 groups (n=7–8) and steroids given on days 0 and 5 subcutaneously, sensitised with 2.5% oxazalone challenged with 0.25%.

Group 1: sensitisation and challenge plus olive oil (positive control).
Group 2: sensitisation and challenge only.
Group 3: sensitisation and challenge plus DHEA (100 µg/mouse).
Group 4: sensitisation and challenge plus DHEAS (100 µg/mouse).
Group 5: sensitisation and challenge plus DEX (100 µg/mouse).

The data are shown in FIG. (5) measured at 24 h post-challenge. Both DHEA and DHEAS significantly augmented the response whereas it was inhibited by DEX. These data are consistent with the role of DHEA and DHEAS as immunostimulants/pro-inflammatories in vivo and DEX as immunosuppressive/anti-inflammatory.

By ANOVA **$p<0.05$ vs control+dexamethasone
$$p<0.05$ vs control dhea+dheas

EXPERIMENT 3

Anti-glucocorticoid Effect of DHEA

The data shown in FIG. 6 indicate that by increasing the administered dose of DHEAS (and thereby its conversion to DHEA) a functional anti-glucocorticoid effect of DHEA exists in this model.

Steroids given on day 0 and 4 subcutaneously in dmso 20%: olive oil 80%.

Sensitised with 2.5% oxazalone challenged with 0.25%. Results presented as mean±sem, n=10.

EXPERIMENT 4

Effect of Sulphatase Inhibition

Animals were randomised into 9 groups (n=7) and steroids given on days 0 and 4 subcutaneously sensitised with 2.5% oxazalone challenged with 0.25%. Results given as mean±sem, n=7.
Group 1: sensitisation and challenge plus olive oil (positive control)
Group 2: sensitisation and challenge plus DEX (5 mg/kg)
Group 3: sensitisation and challenge plus DHEA (5 mg/kg)
Group 4: sensitisation and challenge plus DHEA (5 mg/kg) and CT2251 (0.1 mg/kg)
Group 5: sensitisation and challenge plus DHEA (5 mg/kg) and CT2251 (10 mg/kg)
Group 6: sensitisation and challenge plus CT2251 (0.1 mg/kg)
Group 7: sensitisation and challenge plus CT2251 (10 mg/kg)
Group 8: sensitisation and challenge plus DHEAS (5 mg/kg)
Group 9: sensitisation and challenge plus DHEAS (5 mg/kg) and CT2251 (0.1 mg/kg)
Group 10: sensitisation and challenge plus DHEAS (5 mg/kg) and CT2251 (10 mg/kg)

The data using these relatively weak inhibitors are shown in FIG. (7). Both DHEA and DHEAS augmented the normal ear swelling whereas it was inhibited by DEX. CT2251 (at both doses) reversed the augmentation seen with DHEAS but not that seen with DHEA. CT2251 on its own (at both doses) significantly inhibited the normal ear swelling response. These data show that inhibition of steroid sulphate sulphatase can reverse the stimulatory effect of DHEAS, a substrate for the enzyme. Furthermore, the ear swelling response itself is at least partially dependent on a product of endogenous sulphatase activity such as DHEA since CT2251 administration alone causes an immunosuppressive or anti-inflammatory effect.

EXPERIMENT 5

Effect of CT2251 is Dose-Dependent

Animals were randomised into 8 groups (n=7–14) and steroids given in days 0 and 4, (see FIG. 8). Sensitised with 2.5% oxazalone challenged with 0.25%. Results presented as mean±sem, n=7–14. Timepoint=24 h.
Group 1: sensitisation and challenge plus olive oil (positive control)
Group 2: sensitisation and challenge plus DEX (5 mg/kg)
Group 3: sensitisation and challenge plus CT2251 (0.3 mg/kg)
Group 4: sensitisation and challenge plus CT2251 (0.1 mg/kg)
Group 5: sensitisation and challenge plus CT2251 (0.03 mg/kg)
Group 6: sensitisation and challenge plus CT2251 (0.01 mg/kg)
Group 7: sensitisation and challenge plus CT2251 (0.003 mg/kg)
Group 8: sensitisation and challenge plus CT2251 (0.001 mg/kg)

Dexamethasone inhibited the degree of ear swelling. This was also inhibited by CT2251 treatment in a dose-dependent manner with doses of 0.1 and above being effective.

EXPERIMENT 6

Effect of Substrate on CT2251-Mediated Inhibitory Response

Animals were randomised into 9 groups (n=7–14) and steroids given on days 0 and 4 (see FIG. 9). Sensitised with 2.5% oxazalone challenged with 0.25%. Results presented as mean±sem. Timepoint=24 h.
Group 1: sensitisation and challenge plus olive oil (positive control)
Group 2: sensitisation and challenge plus DEX (5 mg/kg)
Group 3: sensitisation and challenge plus DHEAS (50 mg/kg)
Group 4: sensitisation and challenge plus DHEAS (15 mg/kg)
Group 5: sensitisation and challenge plus DHEAS (5 mg/kg)
Group 6: sensitisation and challenge plus DHEAS (50 mg/kg) and CT2251 (0.1 mg/kg)
Group 7: sensitisation and challenge plus DHEAS (15 mg/kg) and CT2251 (0.1 mg/kg)
Group 8: sensitisation and challenge plus DHEAS (5 mg/kg) and CT2251 (0.1 mg/kg)
Group 9: sensitisation and challenge plus CT2251 (0.1 mg/kg)

The data indicate that the inhibitory effect of CT2251 on the ear swelling response can be reverse by increasing doses of DHEAS, the substrate for the sulphatase enzyme.

EXPERIMENT 7

Effect of DHEAS and Sulphatase Inhibition of Cellular Infiltrate

Animals were randomised into 7 groups (n=7–10) and steroids given on days 0 and 5. At 24 h following challenge, ears were removed, fixed and stained with either an anti-CD3 (T-cells) or anti-Mac-1 (monocytes/macrophages) antibody and the number of positive cells counted in 10 random fields.
Group 1: olive oil only
Group 2: sensitisation and challenge plus olive oil (vehicle control)
Group 3: sensitisation and challenge plus DHEAS (5 mg/kg)
Group 4: sensitisation and challenge plus DHEAS (5 mg/kg) and CT2251 (10 mg/kg)
Group 5: sensitisation and challenge plus CT2251 (10 mg/kg)
Group 6: sensitisation and challenge plus DEX (5 mg/kg)
Group 7: normal ears The data in FIG. (10) show that DHEAS can augment both immune and inflammatory cell infiltrate into challenged ears. This can be effectively reversed by concomitant treatment with CT2251. CT2251 on its own was able to further reduce the number of infiltrating CD3 positive cells. These observations indicate that stimulation or inhibition of steroid sulphate sulphatase can augment or attenuate the movement of both immune and inflammatory cell types into the ears of sensitised mice.
*=$p<0.05$ vs DHEAS
$=$p<0.05$ vs vehicle control
C=$p<0.05$ vs CT2251.

DELAYED TYPE HYPERSENSITIVITY IN THE MOUSE

Animals were randomised into 10 groups (n=7–8) and steroids given on day 0 and 4.
Steroids were given on day 0 and 3 subcutaneously. Response at 24 h post challenge. Results given as mean±sem. $, *$p<0.05$ ANOVA.
Group 1: sensitisation and challenge plus olive oil (positive control)
Group 2: sensitisation and challenge plus DHEA (5 mg/kg)
Group 3: sensitisation and challenge plus DHEAS (5 mg/kg)

Group 4: sensitisation and challenge plus DEX (5 mg/kg)
Group 5: sensitisation and challenge plus DHEA (5 mg/kg) and CT2251 (10 mg/kg)
Group 6: sensitisation and challenge plus DHEA (5 mg/kg) and CT2251 (0.1 mg/kg)
Group 7: sensitisation and challenge plus DHEAS (5 mg/kg) and CT2251 (10 mg/kg)
Group 8: sensitisation and challenge plus DHEAS (5 mg/kg) and CT2251 (0.1 mg/kg)
Group 9: sensitisation and challenge plus CT2251 (10 mg/kg)
Group 10: sensitisation and challenge plus CT2251 (0.1 mg/kg)

The data shown in FIG. (11) are consistent with the observations made in the mouse contact sensitisation model in terms of how DHEA/S, DEX and CT2251 affect the readout. DHEA and DHEAS are clearly pro-immune (or pro-inflammatory) and CT2251 can effectively reverse the DHEAS-mediated augmentation. Also CT2251 on its own can markedly reduce the foot swelling response.

DELAYED TYPE HYPERSENSITIVITY IN THE RAT

Lewis rats were sensitised with SRBC IV and challenged 4 days later with $10^8$SRBC into the footpad. The resulting swelling response was measured 24 and 48 h later. Rats were randomised into 5 groups (n=6–7) and steroids given on days 0, 3 and 4, subcutaneously. Results given as mean±sem.
Group 1: challenge only
Group 2: sensitisation and challenge plus vehicle
Group 3: sensitisation and challenge plus CT2251 (10 mg/kg)
Group 4: sensitisation and challenge plus CT2251 (1 mg/kg)
Group 5: sensitisation and challenge plus CT2251 (0.1 mg/kg)

The data shown in FIG. (12) indicate that CT2251 can also suppress a DTH response in rats.

COLLAGEN II-INDUCED ARTHRITIS IN MICE

Male DBA/1 mice were sensitised with type II collagen into the base of the tail in FCA in day 0. These animals received a further injection of CII in FICA (Freunds Incomplete Adjuvant) on day 18 and incidence and severity of arthritis assessed from day 25. Mice were randomised into 3 groups (n=10).
Group 1: tap water p.o. on day −1 and weekly
Group 2: olive oil p.o. on day −1 and weekly
Group 3: CT2251 (10 mg/kg) on day −1 and weekly The data shown in FIG. (13) shows an incidence of 60 and 40% in the tap water and olive oil treated groups with those getting the disease showing severe signs. Treatment with CT2251 prevented the development of any disease.

CARRAGEENAN PLEURISY

Wistar Rats were anaesthetised and given intra-pleural injections of 0.5% carrageenan in saline at time 0. Six hours later the animals were killed and pleural cavity lavaged with 1 ml. citrated saline. Volume of fluid exudate and exudate cell concentration were measured.

Animals were randomised to 5 treatment groups (n=6).

Results presented as mean±sem, *=sig. diff vs control by ANOVA.
Group 1: olive oil p.o. only
Group 2: DEX (1 mg/kg) p.o. at T=−1 h
Group 3: CT2251 (10 mg/kg) p.o. at T=−24 h and −1 h
Group 4: CT2251 (10 mg/kg) p.o. at t −1h
Group 5: DHEAS (5 mg/kg) p.o. at T=−24 h and −1 h The data shown in FIG. (14) indicate that DEX can completely inhibit fluid leakage and markedly reduce cellular influx (68%). Treatment with CT2251 at −24 h and −1 h significantly reduced both exudate volume (43%) and cell infiltrate (28%) indicating that inhibition of steroid sulphate sulphatase can reduce an inflammatory-based response.

EFFECTS OF PUTATIVE METABOLITES OF DHEAS(S) IN THE CONTACT SENSITISATION MODEL

EXPERIMENT 1

Effect of AED

Animals were randomised to 8 groups (n=10) and steroids given on days 0 and 4 subcutaneously 20% DMSO: 80% olive oil. Sensitised with 2.5% oxazalone challenged with 0.25%.
Group 1: sensitisation and challenge plus vehicle (positive control)
Group 2: sensitisation and challenge plus DHEA (5 mg/kg)
Group 3: sensitisation and challenge plus DHEA (0.5 mg/kg)
Group 4: sensitisation and challenge plus DHEA (0.05 mg/kg)
Group 5: sensitisation and challenge plus DHEA (0.005 mg/kg)
Group 6: sensitisation and challenge plus AED (5 mg/kg)
Group 7: sensitisation and challenge plus AED (0.5 mg/kg)
Group 8: sensitisation and challenge plus AED (0.05 mg/kg)

The data shown in FIG. 15 indicate that AED and DHEA can augment the ear swelling response in this mode. The effect of AED can be seen down to a dose of 0.05 mg/kg or less.

EXPERIMENT 2

Effect of AEDS

Animals were randomised into 10 groups (n=10) and steroids given on days 0 and 4 subcutaneously in DMSO 20%: olive oil 80%. Sensitised with 2.5% oxazalone challenged with 0.25%. Results given as mean±sem.
Group 1: sensitisation and challenge plus vehicle (positive control)
Group 2: sensitisation and challenge plus DHEAS (5 mg/kg)
Group 3: sensitisation and challenge plus DHEAS (0.5 mg/kg)
Group 4: sensitisation and challenge plus DHEAS (0.05 mg/kg)
Group 5: sensitisation and challenge plus DHEAS (0.005 mg/kg)
Group 6: sensitisation and challenge plus AEDS (5 mg/kg)
Group 7: sensitisation and challenge plus AEDS (0.5 mg/kg)
Group 8: sensitisation and challenge plus AEDS (0.05 mg/kg)
Group 9: sensitisation and challenge plus AEDS (0.005 mg/kg)
Group 10: sensitisation and challenge plus AEDS (0.0005 mg/kg)

The data presented in FIG. 16 show that AEDS can augment the ear swelling response in this model. This is achieved at doses at least 1000-fold less than seen with DHEAS.

EXPERIMENT 3

Effect of Sulphatase Inhibition on the Response to AEDS

Animals were randomised into groups (n=10–11) and steroids given in days 0 and 4 subcutaneously in DMSO 20%: olive oil 80%. Sensitised with 2.5% oxazalone challenged with 0.25%. Results given as mean±sem.

Group 1: sensitisation and challenge plus vehicle (positive control)
Group 2: sensitisation and challenge plus AEDS (5 mg/kg)
Group 3: sensitisation and challenge plus AEDS (5 mg/kg) and CT 2251 (0.1 mg/kg)
Group 4: sensitisation and challenge plus DHEAS (5 mg/kg)
Group 5: sensitisation and challenge plus DHEAS (5 mg/kg) and Ct 2251 (0.1 mg/kg)
Group 6: sensitisation and challenge plus CT 2251 (0.1 mg/kg)
Group 7: sensitisation and challenge plus DEX (5 mg/kg)

The data presented in FIG. 17 indicate that the stimulatory response seen with AEDS (and DHEAS) can be inhibited by a sulphatase inhibitor. This shows that AEDS can serve as a physiological substrate for the sulphatase enzyme in vivo.

We claim:

1. A method of treating a human subject having an inflammatory disease comprising administering an effective amount of an inhibitor which prevents the normal physiological effect of DHEA or a physiologically active metabolite of DHEA on inflammatory responses, wherein the inhibitor is a steroid sulphate inhibitor, thereby treating the subject.

2. A method of treating a human subject having an inflammatory disease comprising an effective amount of an inhibitor which prevents the normal physiological effect of DHEA or a physiologically active metabolite of DHEA, wherein the physiologically active metabolite is selected from the group consisting of 70H-DHEA, 70-DHEA-S, 160-DHEA, 160-DHEA-S, androstenediol (AED), AED-S, androstenetriol (AET), AET-S, and DHEA-S on inflammatory responses, wherein the inhibotor is a steroid sulphate sulphatase inhibitor, thereby treating the subject.

3. A method according to claim 1 wherein said steroid sulphate sulphase inhibitor is estrone-3O-N,N-dimethyl) sulphamate.

4. A method according to claim 1, wherein said steroid sulphate sulphatase inhibitor is estrone-3-methylphosphonate.

5. A method according to claim 1, wherein said steroid sulphate sulphatase inhibitor is estrone 3-o-sulphamate.

* * * * *

UNITED STATES PATENT AND TRADEMARK OFFICE
CERTIFICATE OF CORRECTION

PATENT NO : 6,013,642
DATED : January 11, 2000
INVENTOR(S): Roland Foulkes et al It is certified that error appears in the above-identified patent and that said Letters Patent is hereby corrected as shown below:

Claim 1, line 6 of column 23, after "sulphate" insert

--sulphatase--.

Claim 2, line 2 of column 24, after "comprising" insert

--administering--.

Claim 2, line 6 of column 24, delete "7O-DHEAS-S" and insert

--7OH-DHEA-S--.

Claim 2, line 7 of column 24, delete "16O-DHEA, 16O-DHEA-S" and insert

--16OH-DHEA, 16OH-DHEA-S--.

Claim 2, line 9 of column 24, delete "inhibotor" and insert

--inhibitor--.

UNITED STATES PATENT AND TRADEMARK OFFICE
CERTIFICATE OF CORRECTION

PATENT NO. : 6,013,642
DATED : January 11, 2000
INVENTOR(S) : Roland Foulkes, et. al.

It is certified that error appears in the above-identified patent and that said Letters Patent is hereby corrected as shown below:

Claim 3, line 2, column 24, delete "-30-N,N-demethyl)" and insert -- -3-O-(N,N-dimethyl)--.

Signed and Sealed this

Twenty-sixth Day of December, 2000

Attest:

Q. TODD DICKINSON

Attesting Officer

Director of Patents and Trademarks